United States Patent
Stauton et al.

(10) Patent No.: US 11,207,419 B2
(45) Date of Patent: Dec. 28, 2021

(54) CADHERIN-17 SPECIFIC ANTIBODIES AND CYTOTOXIC CELLS FOR CANCER TREATMENT

(71) Applicants: Donald E. Stauton, Kirkland, WA (US); ARBELE LIMITED, Hong Kong (CN)

(72) Inventors: Donald E. Stauton, Kirkland, WA (US); John Moonching Luk, Bellevue, WA (US); Zhijie Li, Shanghai (CN)

(73) Assignee: ARBELE LIMITED, Hong Kong (CN)

( * ) Notice: Subject to any disclaimer, the term of this patent is extended or adjusted under 35 U.S.C. 154(b) by 194 days.

(21) Appl. No.: 16/068,665

(22) PCT Filed: Jan. 7, 2017

(86) PCT No.: PCT/US2017/012648
§ 371 (c)(1),
(2) Date: Jul. 7, 2018

(87) PCT Pub. No.: WO2017/120557
PCT Pub. Date: Jul. 13, 2017

(65) Prior Publication Data
US 2019/0046655 A1 Feb. 14, 2019

Related U.S. Application Data

(60) Provisional application No. 62/276,855, filed on Jan. 9, 2016.

(51) Int. Cl.
| | | |
|---|---|---|
| *A61K 47/68* | (2017.01) | |
| *A61K 39/395* | (2006.01) | |
| *C07K 16/28* | (2006.01) | |
| *A61P 35/00* | (2006.01) | |
| *C12N 15/11* | (2006.01) | |
| *A61K 39/00* | (2006.01) | |

(52) U.S. Cl.
CPC ...... *A61K 47/6803* (2017.08); *A61K 39/3955* (2013.01); *A61P 35/00* (2018.01); *C07K 16/28* (2013.01); *C07K 16/2839* (2013.01); *C12N 15/11* (2013.01); *A61K 2039/505* (2013.01); *A61K 2300/00* (2013.01); *C07K 2317/24* (2013.01); *C07K 2317/622* (2013.01); *C07K 2317/73* (2013.01); *C07K 2317/77* (2013.01); *C07K 2317/92* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 2010/0028357 A1 | 2/2010 | Matsubara et al. |
| 2010/0092978 A1 | 4/2010 | Luk et al. |
| 2014/0322218 A1 | 10/2014 | Xiao et al. |
| 2015/0322151 A1 | 11/2015 | Xiao et al. |

FOREIGN PATENT DOCUMENTS

WO WO2010123874 A 10/2010

OTHER PUBLICATIONS

Wang et al. (PLOS ONE, 8(9): 1-6, 2013).*
Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*

* cited by examiner

*Primary Examiner* — Nelson B Moseley, II
(74) *Attorney, Agent, or Firm* — Wen IP LLC, Zhihua Han

(57) ABSTRACT

Embodiments of the present disclosure relate to cadherin-17 specific antibodies and cytotoxic cells for cancer treatment. For example, an antibody may have specificity for cadherin-17 and include an amino acid sequence having at least 70% similarity with an amino acid sequence selected from SEQ ID NO: 1-21.

19 Claims, 35 Drawing Sheets
Specification includes a Sequence Listing.

| | |
|---|---|
| Lic3 VL | DVLMTQIPLSLTVSLGDQASISCRSSQSIVHSNGNTYLEWYLQRPGQSPKLLI YKVSNRFSGVPDRFSGSGSGTDFTLKISRVEAEDLGVYYCFQGSHVPLTFGA GTKLELK (SEQ ID NO. 1) |
| Lic3 VH | EVQLVESGGGLVKPGGSLKLSCAASGFSFSDYYMYWVRQAPEKRLEWVA SISFDGTYTYYTDRVKGRFTISRDNAKNNLYLQMSSLKSEDTAMYYCAR DRPAWFPYWGQGTLVTVSA (SEQ ID NO. 2) |
| Lic5 VL | DIVLTQTTLSLNVSLGDQASISCRSSQSIVHSNGNTYLEWYLQRPGQSPKLLI YKVSNRFSGVPDRFSGSGSGTDFTLKISRVEAEDLGVYYCFQGSHVPLTFGA GTKLELKRAD (SEQ ID NO. 3) |
| Lic5 VH | EVQLEESGGGLVKPGGSLKLPCAASGSSFSDYYMYWVRQTPEKRLEWVA SISFDGTYTYYTDRVKGRFTISRDNAKNNLYLQMSSLKSEDTAMYYCAR DRPAWFPYWGQGTLVTVSA (SEQ ID NO. 4) |

FIG. 1

```
Lic3VL       DIVLTQTPLSLPVSLGDQASISCRSSQSIVHSNGNTYLGWYLQKPGQSPKLLIYKVSNR
2-30/J1      DIVMTQSPLSLPVTLGQPASISCRSSQSIVHSNGNTYLQWFQQRPGQSPRLLIYKVSNR
             *:*:**:****.*.**:**.*******************:** ****:.***:*****

Hum1         ..........................RSSQSIVHSNG......................KVSNR
Hum2         ...........T..............RSSQSIVHSNG......................KVSNR
Hum3         .......................Q..RSSQSIVHSNG......................KVSNR
Hum4         ..........................RSSQSIVHSNG.................L....KVSNR
Hum5         ..........................RSSQSIVHSNG......................KVSNR
Hum6         ..........................RSSQSIVHSNG......................KVSNR

Lic3VL       FSGVPDRFSGSGSGTDFTLKISRVEAEDLGVYYCFQGSHVPLTFGAGTKLEIK
2-30/J1      FSGVPDRFSGSGSGTDFTLKISRVEAEDVGVYYCFQGSHVPLTFGQGTKVEIK
             ****************************:*****************.**:***

Hum1         FS...............................FQGSHVPLT.........
Hum2         FS...............................FQGSHVPLT.........
Hum3         FS...............................FQGSHVPLT.........
Hum4         FS...............................FQGSHVPLT.........
Hum5         FS...............................FQGSHVPLT.........
Hum6         FS...............................FQGSHVPLT..A......
```

FIG. 2

```
Lic3VL      DIVLTQTPLSLTVSLGDQASISCRSSQSIVHSNGNTYLGWYLQRPGQSPKLLIYKVSNRF
2-24/J1     DIVMTQTPLSSPVTLGQPASISCRSSQSIVHSNGNTYLNWLQQRPGQPPRLLIYKVSNRF
            *:*:*****  :*:  *:; ***********************  ***** *;*******

Hum1        ...................RSSQSIVHSNG.........................KVSNRF
Hum2        ...........L.......RSSQSIVHSNG.........................KVSNRF
Hum3        ............T......RSSQSIVHSNG.........................KVSNRF
Hum4        .................Q.RSSQSIVHSNG.........................KVSNRF
Hum5        ...................RSSQSIVHSNG.............Y...........KVSNRF
Hum6        ...................RSSQSIVHSNG....................S....KVSNRF
Hum7        ...................RSSQSIVHSNG.........................KVSNRF

Lic3VL      SGVPDRFSGSGSGTDFTLKISRVEAEDLGVYYCFQGSHVPLTFGAGTKLELK
2-24/J1     SGVPDRFSGSGAGTDFTLKISRVEAEDVGVYYCFQGSHVPLTFGQGTKVEIK
            ***********;***********************  ***;*;*

Hum1        S...............................FQGSHVPLT..........
Hum2        S...............................FQGSHVPLT..........
Hum3        S...............................FQGSHVPLT..........
Hum4        S...............................FQGSHVPLT..........
Hum5        S...............................FQGSHVPLT..........
Hum6        S...............................FQGSHVPLT..........
Hum7        S...............................FQGSHVPLT..A.......

Lic3Vk      DVLMTQIPLSLTVSLGDQASISCRSSQSIVHSNGNTYLEWYLQRPGQSPKLLIYKVSNRF
Vk2-29      DIVMTQTPLSLSVTPGQPASISCRSSQSIVHSNGNTYLEWYLQKPGQSPQLLIYKVSNRF
            *;:***  ****;*;  *;  ************************;*****;*******

Hum1        ......I.....................RSSQSIVHSNG...............KVSNRF
Hum2        ............L...............RSSQSIVHSNG...............KVSNRF
Hum3        ..............Q.............RSSQSIVHSNG...............KVSNRF
Hum4        ............................RSSQSIVHSNG...........K...KVSNRF
Hum5        ............................RSSQSIVHSNG...............KVSNRF

Lic3Vk      SGVPDRFSGSGSGTDFTLKISRVEAEDLGVYYCFQGSHVPLTFGAGTKLELK
Vk2-29      SGVPDRFSGSGSGTDFTLKISRVEAEDVGVYYCFQGSHVPLTFGAGTKLELK
            ***************************;***********************

Hum1        S...............................FQGSHVPLT..........
Hum2        S...............................FQGSHVPLT..........
Hum3        S...............................FQGSHVPLT..........
Hum4        S...............................FQGSHVPLT..........
Hum5        S....................L..........FQGSHVPLT..........
```

```
lic3VH       QVQLQESGGGLVRPGGSLRLSCAASGFSFSDYYMYWVRQAPEKKLEWVASISFDGTYYYI
3-30/J74     QVQLVESGGGVVQPGRSLRLSCAASGFTFSDYYMHWVRQAPGKGLEWVASISFDGTYYYI
Hum1         ............................................................
Hum2         .....Q......................................................
Hum3         ............................................................
Hum4         ............Q...............................................
Hum5         ............................................................
Hum6         ............................................................
Hum7         ............................................................
Hum8         ............................................................

lic3VH                    ...DYYMY........................SISFDGTYYYI
3-30/J74                  ...DYYMH........................SISFDGTYYYI
Hum1                      ...DYYMY........................SISFDGTYYYI
Hum2                      ...DYYMY........................SISFDGTYYYI
Hum3                      ...DYYMY........................SISFDGTYYYI
Hum4                      ...DYYMY.....E..................SISFDGTYYYI
Hum5                      ...DYYMY.......R................SISFDGTYYYI
Hum6                      ...DYYMY........................SISFDGTYYYI
Hum7                      ...DYYMY........................SISFDGTYYYI
Hum8                      .T.DYYMY........................SISFDGTYYYI lic3VH       TDRVKGRFTISRDNAKNTLYLQMNSLKSEDTAMYYCARDRPAWFPYWGQGTLVTVSA
3-30/J74     TDRVKGRFTISRDNSKNTLYLQMNSLRAEDTAVYYCARDRPAWFPYWGQGTLVTVSA
Hum1         TDRVKG..................................DRPAWFPY........
Hum2         TDRVKG..................................DRPAWFPY........
Hum3         TDRVKG..................................DRPAWFPY........
Hum4         TDRVKG..................................DRPAWFPY........
Hum5         TDRVKG..................................DRPAWFPY........
Hum6         TDRVKG..........N............S..........DRPAWFPY........
Hum7         TDRVKG..................................DRPAWFPY........
Hum8         TDRVKG..................................DRPAWFPY........
```

FIG. 5

```
L1C5VL      DIVLTQTPLSLMVSLGDQASISCRSSQSIVHSNGNTYLEWYLQKPGQSPKLLIYKVSNRF
IGKV2-30    DVVMTQSPLSLPVTLGQPASISCRSSQSLVYSDGNTYLNWFQQRPGQSPRLLIYKVSNRD
             *:::***.***.*:*** * * ************* : :*********  *****:****:

Hum1                                   RSSQSIVHSNGNTYLE               KVSNRF
Hum2                              T   .RSSQSIVHSNGNTYLE               KVSNRF
Hum3                              M    RSSQSIVHSNGNTYLE               KVSNRF
Hum4                              Q    RSSQSIVHSNGNTYLE               KVSNRF
Hum5                                   RSSQSIVHSNGNTYLE               KVSNRF
Hum6                                   RSSQSIVHSNGNTYLE       L       KVSNRD

L1C5VL      SGVPDRFSGSGSGTDFTLKISRVEADDLGVYYCFQGSHVPLTFGAGTKLELKRAD
IGKV2-30    SGVPDRFSGSGSGTDFTLKISRVEAEDVGVYYCMQGTHWPVTFGGGTKLEIK---
             ********************************  ** * :**..*** *::

Hum1                                          FQGSHVPLT
Hum2                                          FQGSHVPLT
Hum3                                          FQGSHVPLT
Hum4                                          FQGSHVPLT
Hum5                                          FQGSHVPLT
Hum6                                          FQGSHVPLT
```

FIG. 6

```
Lic5VL   -DIVLTQTTPLSLMVSLGDQASISCRSSQSIVHSNGNTYLEWYLQRPGQSPKLLIYKVSNR
4X0K     KDIVMTQTPSSLPVSLGDQASISCRSSQSIVHSNGNTYLEWYLQKPGQSPKLLIYKVSNR
          **:*:******.******************************:****************
Hum1     ........................................................KVSNR
Hum2     .......T...............................RSSQSIVHSNGNTYLE.....KVSNR
Hum3     .......................................RSSQSIVHSNGNTYLE.....KVSNR
Hum4     .......T..M............................RSSQSIVHSNGNTYLE.....KVSNR
Hum5     .......................................RSSQSIVHSNGNTYLE.....KVSNR
Hum6     .......T..M............................RSSQSIVHSNGNTYLE.....KVSNR

Lic5VL   FSGVPDRFSGSGSGTDFTLKISRVEAEDLGVYYCFQGSHVPLTFGAGTKLELKRAD
4X0K     FSGVPDRFSGSGSGTDFTLKISRVEAEDLGVYYCFQGSHVPPTFGAGTKLELARGA
         ********************************* ****** ********* *  
Hum1     FS...............................FQGSHVPLT............
Hum2     FS...............................FQGSHVPLT............
Hum3     FS...............................FQGSHVPLT............
Hum4     FS...............................FQGSHVPLT............
Hum5     FS...............................FQGSHVPLT............
Hum6     FS...............................FQGSHVPLT............
```

FIG. 7

```
Lic5VH     EVQLVESGGGLVKPGGSLKLSCAASGSFSFSDFYMYWVRQTPEKRLEWVASISFDGTYTYY
IGHV3-21   EVQLVESGGGLVKPGGSLRLSCAASGFTFSSYSMNWVRQAPGKGLEWVSSISSSSSYIYY
           ******************:*****.:*** *:.**** *.***:  *** .::*:*
Hum1       ..........................:.....DFYMY...............SISFDGTYTYY
Hum2       .........................E.......DFYMY...............SISFDGTYTYY
Hum3       ..........................P......DFYMY.....S.........SISFDGTYTYY
Hum4       ..................................DFYMY...............SISFDGTYTYY
Hum5       ..................................DFYMY...............SISFDGTYTYY
Hum6       ..........................P......DFYMY.......E.......SISFDGTYTYY
Hum7       ..................................DFYMY.......R.......SISFDGTYTYY
Hum8       .........................E.......DFYMY.....E.R.......SISFDGTYTYY

Lic5VH     TDRVKGRFTISRDNAKNMLYLQMSSLKSEDTAMYYCARDRPAWFPYWGQGTLVTVSA
IGHV3-21   ADSVKGRFTISRDNAKNSLYLQMNSLRAEDTAVYYCARDRPAWFPYWGQGTLVTVSA
           :*.**************:*****.**:.***:*************************
Hum1       TDRVKG...................................DRPAWFPY.........
Hum2       TDRVKG...................................DRPAWFPY.........
Hum3       TDRVKG...................................DRPAWFPY.........
Hum4       TDRVKG...................................DRPAWFPY.........
Hum5       TDRVKG...................................DRPAWFPY.........
Hum6       TDRVKG...................................DRPAWFPY.........
Hum7       TDRVKG...................................DRPAWFPY.........
Hum8       TDRVKG...................................DRPAWFPY.........
```

| HuLica26 | VH (SEQ ID NO. 5): |
| | AEVQLVETGGGLVQPGRSLRLSCAASGFTFSSYGMHWVRQAPGKGLEWVA |
| | VISYDGSNKYYADSVKGRFTISRDNSKNTLYLQMNSLRAEDTAVYYCASRF |
| | GMDVWGQGT |
| | VL (SEQ ID NO. 6): |
| | MFVMSQSPLSLPVTLGQPASISCRSSQSLVHSDGNTYLSWFQQRPGQSPRRL |
| | IYNVFNRDSGVPDRFSGSGSGTDFTLEISRVEAEDVGVYYCMQGTHWPFTF |
| | GQGTKLE |
| HuLica 30 | VH (SEQ ID NO. 7): |
| | AEVQLVESGGGVVQPGRSLRLSCAASGFTFSSYGMHWVRQAPGKGLEWVA |
| | VISYDGSNKYYADSVKGRFTISRDNSKNTLYLQMNSLRAEDTAVYYCAKGR |
| | WFDPWGQGT |
| | VL (SEQ ID NO. 8): |
| | SVVTQPPSVSGAPGQRVTISCTGSSSNIGAGYGVQWYQQFPGTAPKLLIYG |
| | NNNRPSGVPDRFSGSKSDTSASLAITGLRAEDEADYYCQSYDSSLSGWVFGGG |
| HuLica 66 | VH (SEQ ID NO. 9): |
| | AEVQLVQSGGGVVQPGRSLRLSCAASGFTFSSYGMHWVRQAPGKGLEW |
| | VAVISYDGSNKYYADSVKGRFTISRDNSKNTLYLQMNSLRAEDTAVYYC |
| | AQGSGWYYWQQGT |
| | VL (SEQ ID NO. 10): |
| | DVVMTQSPLSLPVTLGQPASISCRSSRGLVHSDGNTYLTWFQQRPGQSPRR |
| | LIYKVSSRDSGVPDRFSGSGSGTDFTLKINRVEAEDVGVYYCMQGTHWPW |
| | TFGQGTKVE |

FIG. 12

| HuLica 78 | VH (SEQ ID NO. 11): AEVQLVESGSELKKPGASVKVSCKASGYTFNRYAMNWVRQAPGQGL EWMGWINTNTGNPTYAQGFTGRFVFSLDTSVSTAYLQISSLKAEDTAVYY CARGRRGAFDIWGQGT |
|---|---|
| | VL (SEQ ID NO. 12): IVLTQSPLSLPVTPGEPASISCRSSQSLLHRNGYNYLDWYLQKPGQSPQLLIY LGSNRASGVPDRFSGSGSGTDFTLQISRVEAEDVGVYYCMQALLTPRTFGQ GTKVEI |
| HuLica 85 | VH (SEQ ID NO. 13): AEVQLVQSGGGVVQPGRSLRLSCAASGFTFSSYAMHWVRQAPGKGLEWV AVISYDGSNKYYADSVKGRFTISRDNSKNTLYLQMNSLRAEDTAVYYCAR SYSNFDYWGQGT |
| | VL (SEQ ID NO. 14): DVVMTQSPLSLPVTLGQPASISCRSSRSLVYSDGSTYLNWYQQRPGQSPRRL IYKVSNRDAGVPDRFSGSGSATYFTLKISRVEAEDVGVYFCMQGTHWPWTF GQGTKVE |
| HuLica 94 | VH (SEQ ID NO. 15): AEVQLVQSGGGVVQPGRSLRLSCAASGFTFSSYGMHWVRQAPGKGLEWVA VISYDGSNKYYADSVKGRFTISRDNSKNTLYLQMNSLRAEDTAVYYCAQGS GWYYWGQGT |
| | VL (SEQ ID NO. 16): DVVMTQSPLSLPVTLGQPASISCRSSRGLVHSDGNTYLTWFQQRPGQSPRRL IYKVSSRDSGVPDRFSGSGSGTDFTLKINRVEAEDVGVYYCMQGTHWPWT FGQGTKVE |

FIG. 12 (CONTINUED)

CDH17 arm:
QVQLVESGGGVVQPGRSLRLSCAASGFTFSDYYMYWVRQAPGKGLEWVASISFDGT
YTYYTDRVKGRFTISRDNSKNTLYLQMNSLRAEDTAVYYCARDRPAWFPYWGQGTLV
TVSAGGGGSGGGGSGGGGSGDIVMTQTPLSLSVTPGQPASISCRSSQSIVHSNGNTY
LEWYLQKPGQSPQLLIYKVSNRFSGVPDRFSGSGSGTDFTLKISRVEAEDVGVYYCFQG
SHVPLTFGAGTKLELKGAPGGGSGEPKSCDKTHTCPPCPAPELLGGPSVFLFPPKPKDTL
MISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSPEEMTKNQVSLYC
LVKGFYPSDIAVEWESNGQPENNYKTTPPVLDSDGSFFLYSRLTVDKSRWQEGNVFSCS
VMHEALHNHYTQKSLSLSLGK** (SEQ ID NO. 17)

CD3 arm:
EVQLVESGGGLVQPGGSLRLSCAASGYSFTGYTMNWVRQAPGKGLEWVALI
NPYKGVTTYADSVKGRFTISVDKSKNTAYLQMNSLRAEDTAVYYCARSGYYG
DSDWYFDVWGQGTLVTVSSGGGGSGGGGSGGGGSDIQMTQSPSSLSASVGDRV
TITCRASQDIRNYLNWYQQKPGKAPKLLIYYTSRLESGVPSRFSGSGSGTDYTL
TISSLQPEDFATYYCQQGNTLPWTFGQGTKVEIKRTGAPGGGSGEPKSCDKTHTCPPCPAPELL
GGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTL
PPSPEEMTKNQVSLTCLVKGFYPSDIAVEWESNGQPENNYKTTPPVLDSDGSFFLTSRL
TVDKSRWQEGNVFSCSVMHEALHNHYTQKSLSLSLGK** (SEQ ID NO 18)

FIG. 14

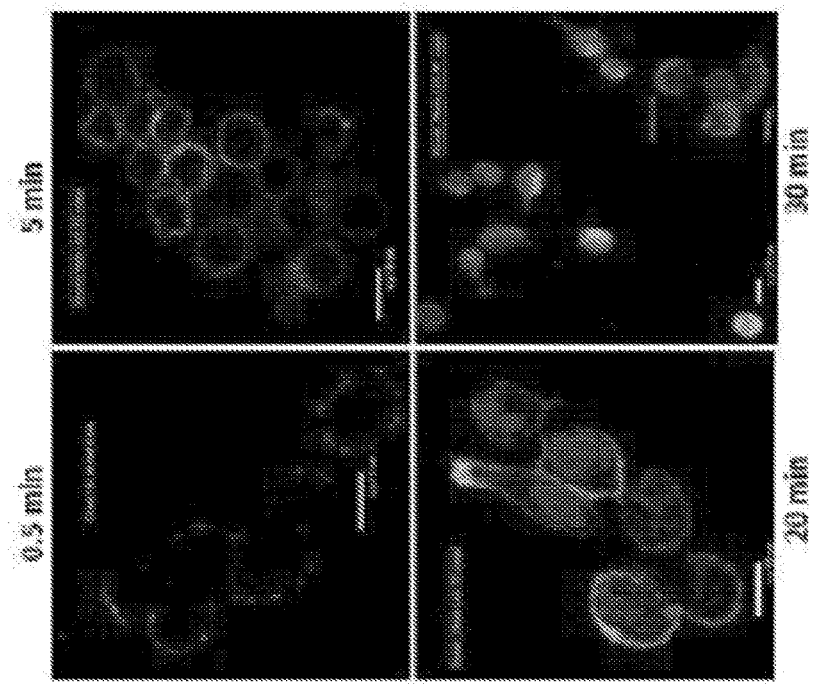
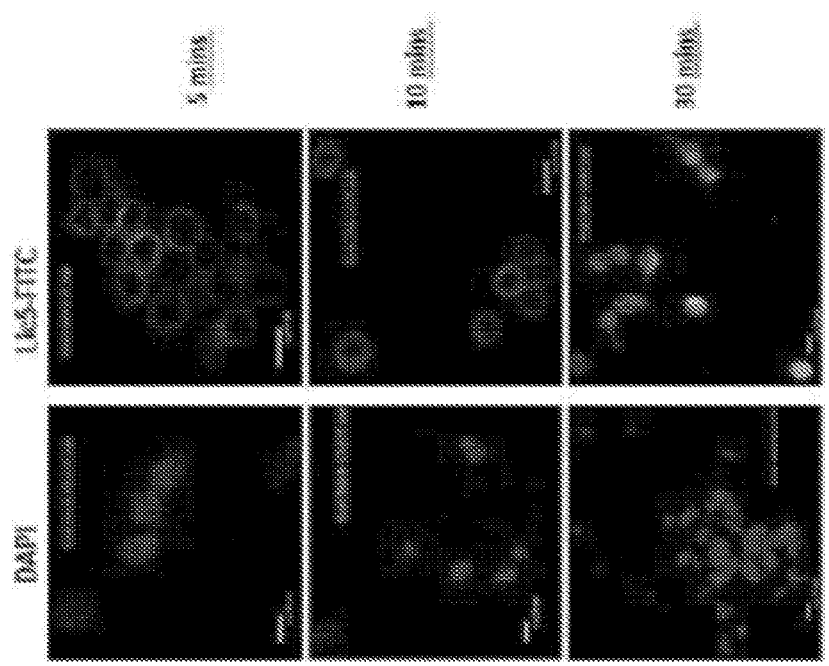
FIG. 18

Examples of CDH17 monoclonal antibodies binding to CDH17 and CDH17 truncates

| | 1E12 | 5F6 | 6C2 | 8E8 | 9A6 | 2H11 | 8G3 | 9C6 | 9F10 | 10C12 | 7C5-C10 | 8G5-A4 | 9B5-G2 |
|---|---|---|---|---|---|---|---|---|---|---|---|---|---|
| BSA | 0.093 | 0.069 | 0.061 | 0.130 | 0.063 | 0.061 | 0.063 | 0.070 | 0.062 | 0.071 | 0.065 | 0.058 | 0.057 |
| CDH17 D1-2 | 0.062 | 0.059 | 0.057 | 0.059 | 0.056 | 0.531 | 0.057 | 0.053 | 0.064 | 0.309 | 0.056 | 0.080 | 0.069 |
| CDH17 D3-4 | 0.061 | 0.063 | 0.063 | 0.058 | 1.151 | 0.057 | 0.061 | 0.054 | 1.333 | 0.055 | 0.054 | 0.054 | 0.058 |
| CDH17 D5-7 | 0.061 | 1.445 | 0.059 | 0.060 | 0.065 | 0.058 | 0.056 | 0.056 | 0.056 | 0.060 | 0.059 | 0.054 | 0.059 |
| CDH17 D6 | 0.062 | 1.403 | 0.070 | 0.061 | 0.058 | 0.058 | 0.056 | 0.058 | 0.057 | 0.055 | 0.057 | 0.059 | 0.061 |
| CHO CDH17F c | 0.158 | 1.334 | 0.618 | 0.152 | 1.095 | 1.365 | 0.613 | 0.434 | 1.306 | 0.428 | 1.003 | 0.717 | 0.602 |
| 293F CDH17F c | 1.029 | 1.556 | 0.879 | 0.972 | 1.081 | 1.511 | 0.655 | 0.556 | 1.097 | 0.357 | 0.927 | 0.744 | 0.053 |
| IgG control | 0.071 | 0.068 | 0.063 | 0.061 | 0.066 | 0.061 | 0.062 | 0.061 | 0.064 | 0.060 | 0.068 | 0.065 | 0.055 |

FIG. 19

SEQ ID NO. 25: hLic3 CAR7a

QVQLVESGGGVVQPGRSLRLSCAASGFTFSDYYMYWVRQAPGKGLEWVASISFDGTYTYYTDRVKGRFTISRDNSKNT
LYLQMNSLRAEDTAVYYCARDRPAWFPYWGQGTLVTVSAGGGGSGGGGSGGGGSGDIVMTQTPLSLSVTPGQPASI
SCRSSQSIVHSNGNTYLEWYLQKPGQSPQLLIYKVSNRFSGVPDRFSGSGSGTDFTLKISRVEAEDVGVYYCFQGSHVPL
TFGAGTKLELKGAPTTTPAPRPPTPAPTIASQPLSLRPEACRPAAGGAVHTRGLDFACDIYIWAPLAGTCGVLLLSLVITLY
CKRGRKKLLYIFKQPFMRPVQTTQEEDGCSCRFPEEEEGGCELRVKFSRSADAPAYQQGQNQLYNELNLGRREEYDVLD
KRRGRDPEMGGKPQRRKNPQEGLYNELQKDKMAEAYSEIGMKGERRRGKGHDGLYQGLSTATKDTYDALHMQALP
PR

SEQ ID NO. 26: hLic3 CAR7b

QVQLVESGGGVVQPGRSLRLSCAASGFTFSDYYMYWVRQAPGKGLEWVASISFDGTYTYYTDRVKGRFTISRDNSKNT
LYLQMNSLRAEDTAVYYCARDRPAWFPYWGQGTLVTVSAGGGGSGGGGSGGGGSGDIVMTQTPLSLSVTPGQPASI
SCRSSQSIVHSNGNTYLEWYLQKPGQSPQLLIYKVSNRFSGVPDRFSGSGSGTDFTLKISRVEAEDVGVYYCFQGSHVPL
TFGAGTKLELKGAPTTTPAPRPPTPAPTIASQPLSLRPEACRPAAGGAVHTRGLDFACDIYIWAPLAGTCGVLLLSLVITLY
CKRGRKKLLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQALPP
R

SEQ ID NO. 27: hLic3 CAR8

QVQLVESGGGVVQPGRSLRLSCAASGFTFSDYYMYWVRQAPGKGLEWVASISFDGTYTYYTDRVKGRFTISRDNSKNT
LYLQMNSLRAEDTAVYYCARDRPAWFPYWGQGTLVTVSAGGGGSGGGGSGGGGSGDIVMTQTPLSLSVTPGQPASI
SCRSSQSIVHSNGNTYLEWYLQKPGQSPQLLIYKVSNRFSGVPDRFSGSGSGTDFTLKISRVEAEDVGVYYCFQGSHVPL
TFGAGTKLELKGAPTTTPAPRPPTPAPTIASQPLSLRPEACRPAAGGAVHTRGLDFACDIYIWAPLAGTCGVLLLSLVITLY
CRSKRSRGGHSDYMNMTPRRPGPTRKHYQPYAPPRDFAAYRSRVKFSRSADAPAYQQGQNQLYNELNLGRREEYDV
LDKRRGRDPEMGGKPQRRKNPQEGLYNELQKDKMAEAYSEIGMKGERRRGKGHDGLYQGLSTATKDTYDALHMQA
LPPR

SEQ ID NO. 28: hLic3 CAR9

QVQLVESGGGVVQPGRSLRLSCAASGFTFSDYYMYWVRQAPGKGLEWVASISFDGTYTYYTDRVKGRFTISRDNSKNT
LYLQMNSLRAEDTAVYYCARDRPAWFPYWGQGTLVTVSAGGGGSGGGGSGGGGSGDIVMTQTPLSLSVTPGQPASI
SCRSSQSIVHSNGNTYLEWYLQKPGQSPQLLIYKVSNRFSGVPDRFSGSGSGTDFTLKISRVEAEDVGVYYCFQGSHVPL
TFGAGTKLELKGAPGGGSEPKSSDKTHTCPPCPAPELLGGPDFWVLVVVGGVLACYSLLVTVAFIIFWVKRGRKKLLYIF
KQPFMRPVQTTQEEDGCSCRFPEEEEGGCELRVKFSRSADAPAYQQGQNQLYNELNLGRREEYDVLDKRRGRDPEM
GGKPQRRKNPQEGLYNELQKDKMAEAYSEIGMKGERRRGKGHDGLYQGLSTATKDTYDALHMQALPPR

SEQ ID NO. 19: Lic3 2nd generation CAR (Lic3scFv-CD28hinge+TM+endo-CD3zeta endo)

QVQLQESGGGLVKPGGSLKLSCAASGFSFSDYYMWVRQAPEKRLEWVASISFDGTYTYYTDRVKGRFTISRDNAKN
NLVLQMSSLKSEDTAMYYCARDRPAWFPYWGQGTLVTVSAGGGSGGGGSGGGGSDIVLTQTPLSLTVSLGDQASIS
CRSSQSIVHSNGNTYLGWYLQRPGQSPKLLIYKVSNRFSGVPDRFSGSGSGTDFTLKISRVEAEDLGVYYCFQGSHVPLT
FGAGTKLELKRADLCPSPLFPGPSKPFWVLVVVGGVLACYSLLVTVAFIIFWVRSKRSRLLHSDYMNMTPRRPGPTRK
HYQPYAPPRDFAAYRS(e)GRVKFSRSADAPAYQQGQNQLYNELNLGRREEYDVLDKRRGRDPEMGGKPQRRKNP
QEGLYNELQKDKMAEAYSEIGMKGERRRGKGHDGLYQGLSTATKDTYDALHMQALPPR

FIG. 24

SEQ ID NO. 20: Lic5 2nd generation CAR (Lic5scFv-CD28hinge+TM+endo-CD3zeta endo)

EVQLEESGGGLVQPGGSLKLPCAASGSFSDFYMVWVRQTPEKRLEWVASISFDGTYYYTDRVKGRFTISRDNAKNN
LYLQMSSLKSEDTAMYYCARDRPAWFPYWGQGTLVTVSAGGGGSGGGGSGGGGSDIVLTQTTLSLNVSLGDQASSC
RSSQSIVHSNGNTYLEWYLQRPGQSPKLLIYKVSNRFSGVPDRFSGSGSGTDFTLKISRVEAEDLGVYYCFQGSHVPLTF
GAGTKLELKRADLQSPLFPGPSKPFTWVLVVVGGVLACYSLLVTVAFIIFWVRSKRSRLLHSDYMNMTPRPGPTRKH
YQPYAPPRDFAAYRSxxxRVKFSRSADAPAYQQGQNQLYNELNLGRREEYDVLDKRRGRDPEMGGKPQRRKNP
QEGLYNELQKDKMAEAYSEIGMKGERRRGKGHDGLYQGLSTATKDTYDALHMQALPPR

FIG. 25

SEQ ID NO. 21: HLic26 2nd generation CAR (Lic26scFv-CD28hinge+TM+endo-CD3zeta endo)

AEVQLVETGGGLVQPGRSLRLSCAASGFTFSSYGMHWVRQAPGKGLEWVAVISYDGSNKYYADSVKGRFTISRDNSK
NTLYLQMNSLRAEDTAVYYCASRPGMDVWGQGTTVTVSSGGGGSGGGGSGGGGSSYELTQPPSVSVSPGQTASITCSGSSSN
IGNNYVSWYQQLPGTAPKLLIYDNNKRPSGIPDRFSGSKSGTSASLAISGLRSEDEADYYCGTWDSSLSAVVFGGGTKLTVL
AAAIEVMHTRGLDFACDIYIWAPLAGTCGVLLLSLVITLYCNHRNRSKRSRLLHSDYMNMTPRRPGPTRKHYQPYA
PPRDFAAYRSGGGRVKFSRSADAPAYQQGQNQLYNELNLGRREEYDVLDKRRGRDPEMGGKPQRRKNPQEGLYN
ELQKDKMAEAYSEIGMKGERRRGKGHDGLYQGLSTATKDTYDALHMQALPPR

FIG. 26

SEQ ID NO. 22: Lic3 3rd generation CAR (Lic3scFv-CD28-4-1BB-CD3zeta endo)

QVQLQESGGGLVKPGGSLKLSCAASGFSFSDYYMYWVRQAPEKRLEWVASISFDGTYYYTDRVKGHFTISRDNAKN
NLYLQMSSLKSEDTAMYYCARDRPAWFPYWGQGTLVTVSAGGGGSGGGGSGGGGSDIVLTQTPLSLTVSLGDQASI
SCRSSQSIVHSNGNTYLGWYLQRPGQSPKLLIYKVSNRFSGVPDRFSGSGSGTDFTLKISRVEAEDLGVYYCFQGSHVP
LTFGAGTKLELKRADLCPSPLFPGPSKPFWVLVVVGGVLACYSLLVTVAFIIFWVRSKRSRLLHSDYMNMTPRRPGPT
RKHYQPYAPPRDFAAYRSGGGRGRKKLLYIFKQPFMRPVQTTQEEDGCSCRFPEEEGGCELGGGRVKFSRSADAP
AYQQGQNQLYNELNLGREEYDVLDKRRGRDPEMGGKPQRRKNPQEGLYNELQKDKMAEAYSEIGMKGERRRG
KGHDGLYQGLSTATKDTYDALHMQALPPR

FIG. 27

SEQ ID NO. 23: Lic5 3rd generation CAR (Lic5scFv-CD28hinge+TM+endo-4-1BB endo-CD3zeta endo)

EVQLEESGGGLVKPGGSLKLPCAASGSFSDFYMYWVRQTPEKRLEWVASISFDGTYTYYTDRVKGRFTISRDNAKNN
LYLQMSSLKSEDTAMYYCARDRPAWFPYWGQGTLVTVSAGGGGSGGGGSGGGGSDIVLTQTLSINVSLGDQASIS
CRSSQSIVHSNGNTYLEWYLQRPGQSPKLLIYKVSNRFSGVPDRFSGSGSGTDFTLKISRVLAEDLGVYYCFQGSHVPL
TFGAGTKLELKRAADLCPSPLFPGPSKPFWVLVVVGGVLACYSLLVTVAFIIFWVRSKRSRLLHSDYMNMTPRRPGPT
RKHYQPYAPPRDFAAYRSGGGRGRKKLLYIFKQPFMRPVQTTQEEDGCSCRFPEEEGGCELGGGRVKFSRSADAP
AYQQGQNQLYNELNLGRREEYDVLDKRRGRDPEMGGKPQRRKNPQEGLYNELQKDKMAEAYSEIGMKGERRRG
KGHDGLYQGLSTATKDTYDALHMQALPPR

FIG. 28

SEQ ID NO. 24: HuLic26 3rd generation CAR (Lic26scFv-CD28hinge+TM+endo-4-1BB endo-CD3zeta endo)

AEVQLVETGGGLVQPGGSLRLSCAASGFTFSSYGMHWVRQAPGKGLEWVAVISYDGSNKYYADSVKGRFTISRDNSK
NTLYLQMNSLRAEDTAVYYCASKFGMDVWGQGTGVTVSSGGGGSGGGGSGGGGSMFVWSGSPLSLPTLGQPASSCRSSQ
SLVHSDGNTYLSWFQQRPGQSPRRLIYKVFNRDSGVPDRFSGSGSGTDFTLEISRVEAEDVGVYYCMQGTHWPFTFG
QGTKLELCPSPLFPGPSKPFWVLVVVGGVLACYSLLVTVAFIIFWVRSKRSRLLHSDYMNMTPRPGPTRKHYQPYA
PPRDFAAYRSGGGRGRKKLLYIFKQPFMRPVQTTQEEDGCSCRFPEEEGGCEL@@RVKFSRSADAPAYQQGQN
QLYNELNLGRREEYDVLDKRRGRDPEMGGKPQRRKMPQEGLYNELQKDKMAEAYSEIGMKGERRRGKGHDGLY
QGLSTATKDTYDALHMQALPPR

FIG. 29

SEQUENCE LISTING

```
<160> NUMBER OF SEQ ID NOS: 30

<210> SEQ ID NO 1
<211> LENGTH: 112
<212> TYPE: PRT
<213> ORGANISM: Artificial Sequence
<220> FEATURE:
<223> OTHER INFORMATION: Lic3 VL

<400> SEQUENCE: 1

Asp Val Leu Met Thr Gln Ile Pro Leu Ser Leu Thr Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 2
<211> LENGTH: 117
<212> TYPE: PRT
<213> ORGANISM: Artificial Sequence
```

<220> FEATURE:
<223> OTHER INFORMATION: Lic3 VH

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Tyr Met Tyr Trp Val Arg Gln Ala Pro Glu Lys Arg Leu Glu Trp Val
        35                  40                  45

Ala Ser Ile Ser Phe Asp Gly Thr Tyr Thr Tyr Thr Asp Arg Val
50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala
        115

<210> SEQ ID NO 3
<211> LENGTH: 115
<212> TYPE: PRT
<213> ORGANISM: Artificial Sequence
<220> FEATURE:
<223> OTHER INFORMATION: Lic5 VL

<400> SEQUENCE: 3

Asp Ile Val Leu Thr Gln Thr Thr Leu Ser Leu Asn Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp
        115

<210> SEQ ID NO 4
<211> LENGTH: 117
<212> TYPE: PRT
<213> ORGANISM: Artificial Sequence
<220> FEATURE:
<223> OTHER INFORMATION: Lic5 VH

<400> SEQUENCE: 4

Glu Val Gln Leu Glu Glu Ser Gly Gly Gly Leu Val Lys Pro Gly Gly
1               5                   10                  15

Ser Leu Lys Leu Pro Cys Ala Ala Ser Gly Ser Ser Phe Ser Asp Phe
            20                  25                  30

```
Tyr Met Tyr Trp Val Arg Gln Thr Pro Glu Lys Arg Leu Glu Trp Val
            35                  40                  45

Ala Ser Ile Ser Phe Asp Gly Thr Tyr Thr Tyr Tyr Thr Asp Arg Val
 50                  55                  60

Lys Gly Arg Phe Thr Ile Ser Arg Asp Asn Ala Lys Asn Asn Leu Tyr
 65                  70                  75                  80

Leu Gln Met Ser Ser Leu Lys Ser Glu Asp Thr Ala Met Tyr Tyr Cys
                 85                  90                  95

Ala Arg Asp Arg Pro Ala Trp Phe Pro Tyr Trp Gly Gln Gly Thr Leu
            100                 105                 110

Val Thr Val Ser Ala
            115

<210> SEQ ID NO 5
<211> LENGTH: 110
<212> TYPE: PRT
<213> ORGANISM: Artificial Sequence
<220> FEATURE:
<223> OTHER INFORMATION: HuLica26 VH

<400> SEQUENCE: 5

Ala Glu Val Gln Leu Val Glu Thr Gly Gly Gly Leu Val Gln Pro Gly
 1               5                  10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
            35                  40                  45

Val Ala Val Ile Ser Tyr Asp Gly Ser Asn Lys Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Ser Arg Phe Gly Met Asp Val Trp Gly Gln Gly Thr
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: HuLica26 VL

<400> SEQUENCE: 6

Met Phe Val Met Ser Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Phe Gln Gln Arg Pro Gly Gln Ser
            35                  40                  45

Pro Arg Arg Leu Ile Tyr Asn Val Phe Asn Arg Asp Ser Gly Val Pro
 50                  55                  60

Asp Arg Phe Ser Gly Ser Gly Ser Gly Thr Asp Phe Thr Leu Glu Ile
 65                  70                  75                  80

Ser Arg Val Glu Ala Glu Asp Val Gly Val Tyr Tyr Cys Met Gln Gly
                 85                  90                  95

Thr His Trp Pro Phe Thr Phe Gly Gln Gly Thr Lys Leu Glu
            100                 105                 110
```

<210> SEQ ID NO 7
<211> LENGTH: 110
<212> TYPE: PRT
<213> ORGANISM: Artificial Sequence
<220> FEATURE:
<223> OTHER INFORMATION: HuLica30 VH

<400> SEQUENCE: 7

Ala Glu Val Gln Leu Val Glu Ser Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Val Ile Ser Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Gly Arg Trp Phe Asp Pro Trp Gly Gln Gly Thr
            100                 105                 110

<210> SEQ ID NO 8
<211> LENGTH: 104
<212> TYPE: PRT
<213> ORGANISM: Artificial Sequence
<220> FEATURE:
<223> OTHER INFORMATION: HuLica30 VL

<400> SEQUENCE: 8

Ser Val Val Thr Gln Pro Pro Ser Val Ser Gly Ala Pro Gly Gln Arg
1               5                   10                  15

Val Thr Ile Ser Cys Thr Gly Ser Ser Ser Asn Ile Gly Ala Gly Tyr
            20                  25                  30

Gly Val Gln Trp Tyr Gln Gln Phe Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Asp Thr Ser Ala Ser Leu Ala Ile Thr Gly Leu Arg
65                  70                  75                  80

Ala Glu Asp Glu Ala Asp Tyr Tyr Cys Gln Ser Tyr Asp Ser Ser Leu
                85                  90                  95

Ser Gly Trp Val Phe Gly Gly Gly
            100

<210> SEQ ID NO 9
<211> LENGTH: 110
<212> TYPE: PRT
<213> ORGANISM: Artificial Sequence
<220> FEATURE:
<223> OTHER INFORMATION: HuLica66 VH

<400> SEQUENCE: 9

Ala Glu Val Gln Leu Val Gln Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

```
Tyr Gly Met His Trp Val Arg Gln Ala Pro Gly Lys Gly Leu Glu Trp
            35                  40                  45

Val Ala Val Ile Ser Tyr Asp Gly Ser Asn Lys Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Gln Gly Ser Gly Trp Tyr Tyr Trp Gly Gln Gly Thr
                100                 105                 110

<210> SEQ ID NO 10
<211> LENGTH: 110
<212> TYPE: PRT
<213> ORGANISM: Artificial Sequence
<220> FEATURE:
<223> OTHER INFORMATION: HuLica66 VL

<400> SEQUENCE: 10

Asp Val Val Met Thr Gln Ser Pro Leu Ser Leu Pro Val Thr Leu Gly
 1               5                  10                  15

Gln Pro Ala Ser Ile Ser Cys Arg Ser Ser Arg Gly Leu Val His Ser
             20                  25                  30

Asp Gly Asn Thr Tyr Leu Thr Trp Phe Gln Gln Arg Pro Gly Gln Ser
             35                  40                  45

Pro Arg Arg Leu Ile Tyr Lys Val Ser Ser Arg Asp Ser Gly Val Pro
 50                  55                  60

Asp Arg Phe Ser Gly Ser Gly Ser Gly Thr Asp Phe Thr Leu Lys Ile
 65                  70                  75                  80

Asn Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Glu
                100                 105                 110

<210> SEQ ID NO 11
<211> LENGTH: 112
<212> TYPE: PRT
<213> ORGANISM: Artificial Sequence
<220> FEATURE:
<223> OTHER INFORMATION: HuLica78 VH

<400> SEQUENCE: 11

Ala Glu Val Gln Leu Val Glu Ser Gly Ser Glu Leu Lys Lys Pro Gly
 1               5                  10                  15

Ala Ser Val Lys Val Ser Cys Lys Ala Ser Gly Tyr Thr Phe Asn Arg
             20                  25                  30

Tyr Ala Met Asn Trp Val Arg Gln Ala Pro Gly Gln Gly Leu Glu Trp
            35                  40                  45

Met Gly Trp Ile Asn Thr Asn Thr Gly Asn Pro Thr Tyr Ala Gln Gly
 50                  55                  60

Phe Thr Gly Arg Phe Val Phe Ser Leu Asp Thr Ser Val Ser Thr Ala
 65                  70                  75                  80

Tyr Leu Gln Ile Ser Ser Leu Lys Ala Glu Asp Thr Ala Val Tyr Tyr
                 85                  90                  95

Cys Ala Arg Gly Arg Gly Ala Phe Asp Ile Trp Gly Gln Gly Thr
                100                 105                 110

<210> SEQ ID NO 12
```

<211> LENGTH: 110
<212> TYPE: PRT
<213> ORGANISM: Artificial Sequence
<220> FEATURE:
<223> OTHER INFORMATION: HuLica78 VL

<400> SEQUENCE: 12

Ile Val Leu Thr Gln Ser Pro Leu Ser Leu Pro Val Thr Pro Gly Glu
1               5                   10                  15

Pro Ala Ser Ile Ser Cys Arg Ser Ser Gln Ser Leu Leu His Arg Asn
                20                  25                  30

Gly Tyr Asn Tyr Leu Asp Trp Tyr Leu Gln Lys Pro Gly Gln Ser Pro
            35                  40                  45

Gln Leu Leu Ile Tyr Leu Gly Ser Asn Arg Ala Ser Gly Val Pro Asp
    50                  55                  60

Arg Phe Ser Gly Ser Gly Ser Gly Thr Asp Phe Thr Leu Gln Ile Ser
65                  70                  75                  80

Arg Val Glu Ala Glu Asp Val Gly Val Tyr Tyr Cys Met Gln Ala Leu
                85                  90                  95

Leu Thr Pro Arg Thr Phe Gly Gln Gly Thr Lys Val Glu Ile
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: HuLica85 VH

<400> SEQUENCE: 13

Ala Glu Val Gln Leu Val Gln Ser Gly Gly Gly Val Val Gln Pro Gly
1               5                   10                  15

Arg Ser Leu Arg Leu Ser Cys Ala Ala Ser Gly Phe Thr Phe Ser Ser
                20                  25                  30

Tyr Ala Met His Trp Val Arg Gln Ala Pro Gly Lys Gly Leu Glu Trp
            35                  40                  45

Val Ala Val Ile Ser Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ser Tyr Ser Asn Phe Asp Tyr Trp Gly Gln Gly Thr
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: HuLica85 VL

<400> SEQUENCE: 14

Asp Val Val Met Thr Gln Ser Pro Leu Ser Leu Pro Val Thr Leu Gly
1               5                   10                  15

Gln Pro Ala Ser Ile Ser Cys Arg Ser Ser Arg Ser Leu Val Tyr Ser
                20                  25                  30

Asp Gly Ser Thr Tyr Leu Asn Trp Tyr Gln Gln Arg Pro Gly Gln Ser
            35                  40                  45

```
Pro Arg Leu Ile Tyr Lys Val Ser Asn Arg Asp Ala Gly Val Pro
    50                  55                  60

Asp Arg Phe Ser Gly Ser Gly Ser Ala Thr Tyr Phe Thr Leu Lys Ile
65                  70                  75                  80

Ser Arg Val Glu Ala Glu Asp Val Gly Val Tyr Phe Cys Met Gln Gly
                85                  90                  95

Thr His Trp Pro Trp Thr Phe Gly Gln Gly Thr Lys Val Glu
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: HuLica94 VH

<400> SEQUENCE: 15

Ala Glu Val Gln Leu Val Gln Ser Gly Gly Gly Val Val Gln Pro Gly
1               5                   10                  15

Arg Ser Leu Arg Leu Ser Cys Ala Ala Ser Gly Phe Thr Phe Ser Ser
                20                  25                  30

Tyr Gly Met His Trp Val Arg Gln Ala Pro Gly Lys Gly Leu Glu Trp
            35                  40                  45

Val Ala Val Ile Ser Tyr Asp Gly Ser Asn Lys Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Gln Gly Ser Gly Trp Tyr Tyr Trp Gly Gln Gly Thr
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: HuLica94 VL

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Arg Gly Leu Val His Ser
                20                  25                  30

Asp Gly Asn Thr Tyr Leu Thr Trp Phe Gln Gln Arg Pro Gly Gln Ser
            35                  40                  45

Pro Arg Leu Ile Tyr Lys Val Ser Ser Arg Asp Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu
            100                 105                 110

<210> SEQ ID NO 17
<211> LENGTH: 485
<212> TYPE: PRT
<213> ORGANISM: Artificial Sequence
```

<220> FEATURE:
<223> OTHER INFORMATION: CDH17 arm

<400> SEQUENCE: 17

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ser Ile Ser Phe Asp Gly Thr Tyr Thr Tyr Tyr Thr Asp Arg Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Ser Gly Asp Ile Val Met Thr Gln Thr Pro Leu Ser Leu
    130                 135                 140

Ser Val Thr Pro Gly Gln Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Leu Thr Phe Gly Ala Gly Thr
225                 230                 235                 240

Lys Leu Glu Leu Lys Gly Ala Pro Gly Gly Ser Gly Glu Pro Lys
                245                 250                 255

Ser Cys Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser Gln Glu Asp Pro Glu Val Gln Phe Asn Trp Tyr Val Asp Gly Val
305                 310                 315                 320

Glu Val His Asn Ala Lys Thr Lys Pro Arg Glu Glu Gln Phe Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Gly Leu Pro Ser
        355                 360                 365

Ser Ile Glu Lys Thr Ile Ser Lys Ala Lys Gly Gln Pro Arg Glu Pro
    370                 375                 380

Gln Val Tyr Thr Leu Pro Pro Ser Pro Glu Glu Met Thr Lys Asn Gln
385                 390                 395                 400
```

Val Ser Leu Tyr Cys Leu Val Lys Gly Phe Tyr Pro Ser Asp Ile Ala
            405                 410                 415

Val Glu Trp Glu Ser Asn Gly Gln Pro Glu Asn Asn Tyr Lys Thr Thr
        420                 425                 430

Pro Pro Val Leu Asp Ser Asp Gly Ser Phe Phe Leu Tyr Ser Arg Leu
            435                 440                 445

Thr Val Asp Lys Ser Arg Trp Gln Glu Gly Asn Val Phe Ser Cys Ser
450                 455                 460

Val Met His Glu Ala Leu His Asn His Tyr Thr Gln Lys Ser Leu Ser
465                 470                 475                 480

Leu Ser Leu Gly Lys
            485

<210> SEQ ID NO 18
<211> LENGTH: 486
<212> TYPE: PRT
<213> ORGANISM: Artificial Sequence
<220> FEATURE:
<223> OTHER INFORMATION: CD3 arm

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Thr Thr Tyr Ala Asp Ser Val
    50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Ser Gly Tyr Tyr Gly Asp Ser Asp Trp Tyr Phe Asp Val Trp
        100                 105                 110

Gly Gln Gly Thr Leu Val Thr Val Ser Ser Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Ile Arg Asn Tyr Leu Asn Trp Tyr Gln Gln Lys
                165                 170                 175

Pro Gly Lys Ala Pro Lys Leu Leu Ile Tyr Tyr Thr Ser Arg Leu Glu
            180                 185                 190

Ser Gly Val Pro Ser Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Gly Asn Thr Leu Pro Trp Thr Phe Gly Gln Gly Thr Lys
225                 230                 235                 240

Val Glu Ile Lys Arg Thr Gly Ala Pro Gly Gly Gly Ser Gly Glu Pro
                245                 250                 255

Lys Ser Cys Asp Lys Thr His Thr Cys Pro Pro Cys Pro Ala Pro Glu
            260                 265                 270

```
Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
        290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
        355                 360                 365

Ser Ser Ile Glu Lys Thr Ile Ser Lys Ala Lys Gly Gln Pro Arg Glu
370                 375                 380

Pro Gln Val Tyr Thr Leu Pro Pro Ser Pro Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Thr Ser Arg
        435                 440                 445

Leu Thr Val Asp Lys Ser Arg Trp Gln Glu Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Leu Gly Lys
            485

<210> SEQ ID NO 19
<211> LENGTH: 443
<212> TYPE: PRT
<213> ORGANISM: Artificial Sequence
<220> FEATURE:
<223> OTHER INFORMATION: Lic2 2nd generation CAR

<400> SEQUENCE: 19

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Tyr Met Tyr Trp Val Arg Gln Ala Pro Glu Lys Arg Leu Glu Trp Val
        35                  40                  45

Ala Ser Ile Ser Phe Asp Gly Thr Tyr Thr Tyr Tyr Thr Asp Arg Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
            85                  90                  95

Ala Arg Asp Arg Pro Ala Trp Phe Pro Tyr Trp Gly Gln Gly Thr Leu
        100                 105                 110

Val Thr Val Ser Ala Gly Gly Gly Gly Ser Gly Gly Gly Gly Ser Gly
            115                 120                 125

Gly Gly Gly Ser Asp Ile Val Leu Thr Gln Thr Pro Leu Ser Leu Thr
        130                 135                 140
```

```
Val Ser Leu Gly Asp Gln Ala Ser Ile Ser Cys Arg Ser Gln Ser
145                 150                 155                 160

Ile Val His Ser Asn Gly Asn Thr Tyr Leu Gly Trp Tyr Leu Gln Arg
                165                 170                 175

Pro Gly Gln Ser Pro Lys Leu Leu Ile Tyr Lys Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Leu Gly Val Tyr Tyr
    210                 215                 220

Cys Phe Gln Gly Ser His Val Pro Leu Thr Phe Gly Ala Gly Thr Lys
225                 230                 235                 240

Leu Glu Leu Lys Arg Ala Asp Leu Cys Pro Ser Pro Leu Phe Pro Gly
                245                 250                 255

Pro Ser Lys Pro Phe Trp Val Leu Trp Val Gly Gly Val Leu Ala Cys
            260                 265                 270

Tyr Ser Leu Leu Val Thr Val Ala Phe Leu Leu Phe Trp Val Arg Ser
        275                 280                 285

Lys Arg Ser Arg Leu Leu His Ser Asp Tyr Met Asn Met Thr Pro Arg
    290                 295                 300

Arg Pro Gly Pro Thr Arg Lys His Tyr Gln Pro Tyr Ala Pro Pro Arg
305                 310                 315                 320

Asp Phe Ala Ala Tyr Arg Ser Gly Gly Gly Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
        355                 360                 365

Arg Gly Arg Asp Pro Glu Met Gly Gly Lys Pro Gln Arg Arg Lys Asn
370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
        435                 440

<210> SEQ ID NO 20
<211> LENGTH: 441
<212> TYPE: PRT
<213> ORGANISM: Artificial Sequence
<220> FEATURE:
<223> OTHER INFORMATION: Lic5 2nd generation CAR

<400> SEQUENCE: 20

Glu Val Gln Leu Glu Glu Ser Gly Gly Gly Leu Val Lys Pro Gly Gly
1               5                   10                  15

Ser Leu Lys Leu Pro Cys Ala Ala Ser Gly Ser Ser Phe Ser Asp Phe
                20                  25                  30

Tyr Met Tyr Trp Val Arg Gln Thr Pro Glu Lys Arg Leu Glu Trp Val
            35                  40                  45

Ala Ser Ser Phe Asp Gly Thr Tyr Thr Tyr Tyr Thr Asp Arg Val Lys
50                  55                  60
```

Gly Arg Phe Thr Ile Ser Arg Asp Asn Ala Lys Asn Leu Tyr Leu
65                  70                  75                  80

Gln Met Ser Ser Leu Lys Ser Glu Asp Thr Ala Met Tyr Tyr Cys Ala
            85                  90                  95

Arg Asp Arg Pro Ala Trp Phe Pro Tyr Trp Gly Gln Gly Thr Leu Val
        100                 105                 110

Thr Val Ser Ala Gly Gly Gly Ser Gly Gly Gly Gly Ser Gly Gly
            115                 120                 125

Gly Gly Ser Asp Ile Val Leu Thr Gln Thr Thr Leu Ser Leu Asn Val
130                 135                 140

Ser Gly Asp Gln Ala Ser Ile Ser Cys Arg Ser Ser Gln Ser Ile Val
145                 150                 155                 160

His Ser Asn Gly Asn Thr Tyr Leu Glu Trp Tyr Leu Gln Arg Pro Gly
            165                 170                 175

Gln Ser Pro Lys Leu Leu Ile Tyr Lys Val Ser Asn Arg Phe Ser Gly
        180                 185                 190

Val Pro Asp Arg Phe Ser Gly Ser Gly Ser Gly Thr Asp Phe Thr Leu
    195                 200                 205

Lys Ile Ser Arg Val Glu Ala Glu Asp Leu Gly Val Tyr Tyr Cys Phe
210                 215                 220

Gln Gly Ser His Val Pro Leu Thr Phe Gly Ala Gly Thr Lys Leu Glu
225                 230                 235                 240

Leu Lys Arg Ala Asp Leu Cys Pro Ser Pro Leu Phe Pro Gly Pro Ser
            245                 250                 255

Lys Pro Phe Trp Val Leu Trp Val Gly Val Leu Ala Cys Tyr Ser
        260                 265                 270

Leu Leu Val Thr Val Ala Phe Leu Leu Phe Trp Val Arg Ser Lys Arg
    275                 280                 285

Ser Arg Leu Leu His Ser Asp Tyr Met Asn Met Thr Pro Arg Arg Pro
290                 295                 300

Gly Pro Thr Arg Lys His Tyr Gln Pro Tyr Ala Pro Pro Arg Asp Phe
305                 310                 315                 320

Ala Ala Tyr Arg Ser Gly Gly Gly Arg Val Lys Phe Ser Arg Ser Ala
            325                 330                 335

Asp Ala Pro Ala Tyr Gln Gln Gly Gln Asn Gln Leu Tyr Asn Glu Leu
        340                 345                 350

Asn Leu Gly Arg Arg Glu Glu Tyr Asp Val Leu Asp Lys Arg Arg Gly
    355                 360                 365

Arg Asp Pro Glu Met Gly Gly Lys Pro Gln Arg Arg Lys Asn Pro Gln
370                 375                 380

Glu Gly Leu Tyr Asn Glu Leu Gln Lys Asp Lys Met Ala Glu Ala Val
385                 390                 395                 400

Ser Glu Ile Gly Met Lys Gly Glu Arg Arg Gly Lys Gly His Asp
            405                 410                 415

Gly Leu Val Gln Gly Leu Ser Thr Ala Thr Lys Asp Thr Tyr Asp Ala
        420                 425                 430

Leu His Met Gln Ala Leu Pro Pro Arg
            435                 440

<210> SEQ ID NO 21
<211> LENGTH: 431
<212> TYPE: PRT
<213> ORGANISM: Artificial Sequence
<220> FEATURE:

<223> OTHER INFORMATION: HLic26 2nd generation CAR

<400> SEQUENCE: 21

```
Ala Glu Val Gln Leu Val Glu Thr Gly Gly Gly Leu Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Val Ile Ser Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Val
                85                  90                  95

Cys Ala Ser Arg Phe Gly Met Asp Val Trp Gly Gln Gly Thr Gly Gly
            100                 105                 110

Gly Gly Ser Gly Gly Gly Gly Ser Gly Gly Gly Gly Ser Met Phe Val
        115                 120                 125

Met Ser Gln Ser Pro Leu Ser Leu Pro Val Thr Leu Gly Gln Pro Ala
    130                 135                 140

Ser Ile Ser Cys Arg Ser Gln Ser Leu Val His Ser Asp Gly Asn
145                 150                 155                 160

Thr Tyr Leu Ser Trp Phe Gln Gln Arg Pro Gly Gln Ser Pro Arg Arg
                165                 170                 175

Leu Ile Tyr Asn Val Phe Asn Arg Asp Ser Gly Val Pro Asp Arg Phe
            180                 185                 190

Ser Gly Ser Gly Ser Gly Thr Asp Phe Thr Leu Glu Ile Ser Arg Val
        195                 200                 205

Glu Ala Glu Asp Val Gly Val Tyr Tyr Cys Met Gln Gly Thr His Trp
    210                 215                 220

Pro Phe Thr Phe Gly Gln Gly Thr Lys Leu Glu Leu Cys Pro Ser Pro
225                 230                 235                 240

Leu Phe Pro Gly Pro Ser Lys Pro Phe Trp Val Leu Val Val Gly Gly
                245                 250                 255

Val Leu Ala Cys Tyr Ser Leu Leu Val Thr Val Ala Phe Leu Leu Phe
            260                 265                 270

Trp Val Arg Ser Lys Arg Ser Arg Leu Leu His Ser Asp Tyr Met Asn
        275                 280                 285

Met Thr Pro Arg Arg Pro Gly Pro Thr Arg Lys His Tyr Gln Pro Tyr
    290                 295                 300

Ala Pro Pro Arg Asp Phe Ala Ala Tyr Arg Ser Gly Gly Gly Arg Val
305                 310                 315                 320

Lys Phe Ser Arg Ser Ala Asp Ala Pro Ala Val Gln Gln Gly Gln Asn
                325                 330                 335

Gln Leu Tyr Asn Glu Leu Asn Leu Gly Arg Arg Glu Glu Val Asp Val
            340                 345                 350

Leu Asp Lys Arg Arg Gly Arg Asp Pro Glu Met Gly Gly Lys Pro Gln
        355                 360                 365

Arg Arg Lys Asn Pro Gln Glu Gly Leu Tyr Asn Glu Leu Gln Lys Asp
    370                 375                 380

Lys Met Ala Glu Ala Tyr Ser Glu Ile Gly Met Lys Gly Glu Arg Arg
385                 390                 395                 400
```

Arg Gly Lys Gly His Asp Gly Leu Tyr Gln Gly Leu Ser Thr Ala Thr
            405                 410                 415

Lys Asp Thr Tyr Asp Ala Leu His Met Gln Ala Leu Pro Pro Arg
            420                 425                 430

<210> SEQ ID NO 22
<211> LENGTH: 488
<212> TYPE: PRT
<213> ORGANISM: Artificial Sequence
<220> FEATURE:
<223> OTHER INFORMATION: Lic3 3rd generation CAR

<400> SEQUENCE: 22

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Ser Phe Ser Asp Tyr
            20                  25                  30

Tyr Met Tyr Trp Val Arg Gln Ala Pro Glu Lys Arg Leu Glu Trp Val
        35                  40                  45

Ala Ser Ile Ser Phe Asp Gly Thr Tyr Thr Tyr Tyr Thr Asp Arg Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Asp Ile Val Leu Thr Gln Thr Pro Leu Ser Leu Thr
    130                 135                 140

Val Ser Leu Gly Asp Gln Ala Ser Ile Ser Cys Arg Ser Ser Gln Ser
145                 150                 155                 160

Ile Val His Ser Asn Gly Asn Thr Tyr Leu Gly Trp Tyr Leu Gln Arg
                165                 170                 175

Pro Gly Gln Ser Pro Lys Leu Leu Ile Tyr Lys Val Ser Asn Arg Phe
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Leu Gly Val Tyr Tyr
    210                 215                 220

Cys Phe Gln Gly Ser His Val Pro Leu Thr Phe Gly Ala Gly Thr Lys
225                 230                 235                 240

Leu Glu Leu Lys Arg Ala Asp Leu Cys Pro Ser Pro Leu Phe Pro Gly
                245                 250                 255

Pro Ser Lys Pro Phe Trp Val Leu Val Val Val Gly Gly Val Leu Ala
            260                 265                 270

Cys Tyr Ser Leu Leu Val Thr Val Ala Phe Ile Ile Phe Trp Val Arg
        275                 280                 285

Ser Lys Arg Ser Arg Leu Leu His Ser Asp Tyr Met Asn Met Thr Pro
    290                 295                 300

Arg Arg Pro Gly Pro Thr Arg Lys His Tyr Gln Pro Tyr Ala Pro Pro
305                 310                 315                 320

Arg Asp Phe Ala Ala Tyr Arg Ser Gly Gly Gly Arg Gly Arg Lys Lys
                325                 330                 335

```
Leu Leu Tyr Ile Phe Lys Gln Pro Phe Met Arg Pro Val Gln Thr Thr
                340                 345                 350

Gln Glu Glu Asp Gly Cys Ser Cys Arg Phe Pro Glu Glu Glu Gly
        355                 360                 365

Gly Cys Glu Leu Gly Gly Gly Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 23
<211> LENGTH: 488
<212> TYPE: PRT
<213> ORGANISM: Artificial Sequence
<220> FEATURE:
<223> OTHER INFORMATION: Lic5 3rd generation CAR

<400> SEQUENCE: 23

```
Glu Val Gln Leu Glu Glu Ser Gly Gly Gly Leu Val Lys Pro Gly Gly
1               5                   10                  15

Ser Leu Lys Leu Pro Cys Ala Ala Ser Gly Ser Ser Phe Ser Asp Phe
                20                  25                  30

Tyr Met Tyr Trp Val Arg Gln Thr Pro Glu Lys Arg Leu Glu Trp Val
            35                  40                  45

Ala Ser Ile Ser Phe Asp Gly Thr Tyr Thr Tyr Tyr Thr Asp Arg Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Asp Ile Val Leu Thr Gln Thr Thr Leu Ser Leu Asn
130                 135                 140

Val Ser Leu Gly Asp Gln Ala Ser Ile Ser Cys Arg Ser Ser Gln Ser
145                 150                 155                 160

Ile Val His Ser Asn Gly Asn Thr Tyr Leu Glu Trp Tyr Leu Gln Arg
                165                 170                 175

Pro Gly Gln Ser Pro Lys Leu Leu Ile Tyr Lys Val Ser Asn Arg Phe
            180                 185                 190

Ser Gly Val Pro Asp Arg Phe Ser Gly Ser Gly Ser Gly Thr Asp Phe
        195                 200                 205
```

```
Thr Leu Lys Ile Ser Arg Val Glu Ala Glu Asp Leu Gly Val Tyr Tyr
            210                 215                 220

Cys Phe Gln Gly Ser His Val Pro Leu Thr Phe Gly Ala Gly Thr Lys
225                 230                 235                 240

Leu Glu Leu Lys Arg Ala Asp Leu Cys Pro Ser Pro Leu Phe Pro Gly
                245                 250                 255

Pro Ser Lys Pro Phe Trp Val Leu Val Val Val Gly Gly Val Leu Ala
                260                 265                 270

Cys Tyr Ser Leu Leu Val Thr Val Ala Phe Ile Ile Phe Trp Val Arg
                275                 280                 285

Ser Lys Arg Ser Arg Leu Leu His Ser Asp Tyr Met Asn Met Thr Pro
290                 295                 300

Arg Arg Pro Gly Pro Thr Arg Lys His Tyr Gln Pro Tyr Ala Pro Pro
305                 310                 315                 320

Arg Asp Phe Ala Ala Tyr Arg Ser Gly Gly Arg Gly Arg Lys Lys
                325                 330                 335

Leu Leu Tyr Ile Phe Lys Gln Pro Phe Met Arg Pro Val Gln Thr Thr
                340                 345                 350

Gln Glu Glu Asp Gly Cys Ser Cys Arg Phe Pro Glu Glu Glu Glu Gly
                355                 360                 365

Gly Cys Glu Leu Gly Gly Gly Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Gln Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 24
<211> LENGTH: 476
<212> TYPE: PRT
<213> ORGANISM: Artificial Sequence
<220> FEATURE:
<223> OTHER INFORMATION: HuLic26 3rd generation CAR

<400> SEQUENCE: 24

Ala Glu Val Gln Leu Val Glu Thr Gly Gly Gly Leu Val Gln Pro Gly
1               5                   10                  15

Arg Ser Leu Arg Leu Ser Cys Ala Ala Ser Gly Phe Thr Phe Ser Ser
                20                  25                  30

Tyr Gly Met His Trp Val Arg Gln Ala Pro Gly Lys Gly Leu Glu Trp
                35                  40                  45

Val Ala Val Ile Ser Tyr Asp Gly Ser Asn Lys Tyr Tyr Ala Asp Ser
            50                  55                  60

Val Lys Gly Arg Phe Thr Ile Ser Arg Asp Asn Ser Lys Asn Thr Leu
65                  70                  75                  80
```

-continued

```
Tyr Leu Gln Met Asn Ser Leu Arg Ala Glu Asp Thr Ala Val Tyr Tyr
             85                  90                  95

Cys Ala Ser Arg Phe Gly Met Asp Val Trp Gly Gln Gly Thr Gly Gly
        100                 105                 110

Gly Gly Ser Gly Gly Gly Gly Ser Gly Gly Gly Gly Ser Met Phe Val
        115                 120                 125

Met Ser Gln Ser Pro Leu Ser Leu Pro Val Thr Leu Gly Gln Pro Ala
130                 135                 140

Ser Ile Ser Cys Arg Ser Ser Gln Ser Leu Val His Ser Asp Gly Asn
145                 150                 155                 160

Thr Tyr Leu Ser Trp Phe Gln Gln Arg Pro Gly Gln Ser Pro Arg Arg
                165                 170                 175

Leu Ile Tyr Asn Val Phe Asn Arg Asp Ser Gly Val Pro Asp Arg Phe
            180                 185                 190

Ser Gly Ser Gly Ser Gly Thr Asp Phe Thr Leu Glu Ile Ser Arg Val
        195                 200                 205

Glu Ala Glu Asp Val Gly Val Tyr Tyr Cys Met Gln Gly Thr His Trp
210                 215                 220

Pro Phe Thr Phe Gly Gln Gly Thr Lys Leu Glu Leu Cys Pro Ser Pro
225                 230                 235                 240

Leu Phe Pro Gly Pro Ser Lys Pro Phe Trp Val Leu Val Val Val Gly
                245                 250                 255

Gly Val Leu Ala Cys Tyr Ser Leu Leu Val Thr Val Ala Phe Ile Ile
            260                 265                 270

Phe Trp Val Arg Ser Lys Arg Ser Arg Leu Leu His Ser Asp Tyr Met
        275                 280                 285

Asn Met Thr Pro Arg Arg Pro Gly Pro Thr Arg Lys His Tyr Gln Pro
290                 295                 300

Tyr Ala Pro Pro Arg Asp Phe Ala Ala Tyr Arg Ser Gly Gly Gly Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Gly Gly Gly Arg Val Lys Phe Ser
        355                 360                 365

Arg Ser Ala Asp Ala Pro Ala Tyr Gln Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Gln Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
450                 455                 460

Tyr Asp Ala Leu His Met Gln Ala Leu Pro Pro Arg
465                 470                 475
```

<210> SEQ ID NO 25
<211> LENGTH: 472
<212> TYPE: PRT

<213> ORGANISM: Artificial Sequence
<220> FEATURE:
<223> OTHER INFORMATION: synthesized

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ser Ile Ser Phe Asp Gly Thr Tyr Tyr Tyr Thr Asp Arg Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Ser Gly Asp Ile Val Met Thr Gln Thr Pro Leu Ser Leu
130                 135                 140

Ser Val Thr Pro Gly Gln Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Leu Thr Phe Gly Ala Gly Thr
225                 230                 235                 240

Lys Leu Glu Leu Lys Gly Ala Pro Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg

```
                385                 390                 395                 400
Asp Pro Glu Met Gly Gly Lys Pro Gln Arg Arg Lys Asn Pro Gln Glu
                    405                 410                 415
Gly Leu Tyr Asn Glu Leu Gln Lys Asp Lys Met Ala Glu Ala Tyr Ser
                420                 425                 430
Glu Ile Gly Met Lys Gly Glu Arg Arg Arg Gly Lys Gly His Asp Gly
            435                 440                 445
Leu Tyr Gln Gly Leu Ser Thr Ala Thr Lys Asp Thr Tyr Asp Ala Leu
450                 455                 460
His Met Gln Ala Leu Pro Pro Arg
465                 470

<210> SEQ ID NO 26
<211> LENGTH: 471
<212> TYPE: PRT
<213> ORGANISM: Artificial Sequence
<220> FEATURE:
<223> OTHER INFORMATION: synthesized

<400> SEQUENCE: 26

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asp Tyr
                20                  25                  30
Tyr Met Tyr Trp Val Arg Gln Ala Pro Gly Lys Gly Leu Glu Trp Val
            35                  40                  45
Ala Ser Ile Ser Phe Asp Gly Thr Tyr Thr Tyr Tyr Thr Asp Arg Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Pro Ala Trp Phe Pro Tyr Trp Gly Gln Gly Thr Leu
            100                 105                 110
Val Thr Val Ser Ala Gly Gly Gly Gly Ser Gly Gly Gly Gly Ser Gly
        115                 120                 125
Gly Gly Ser Gly Asp Ile Val Met Thr Gln Thr Pro Leu Ser Leu
130                 135                 140
Ser Val Thr Pro Gly Gln Pro Ala Ser Ile Ser Cys Arg Ser Ser Gln
145                 150                 155                 160
Ser Ile Val His Ser Asn Gly Asn Thr Tyr Leu Glu Trp Tyr Leu Gln
                165                 170                 175
Lys Pro Gly Gln Ser Pro Gln Leu Leu Ile Tyr Lys Val Ser Asn Arg
            180                 185                 190
Phe Ser Gly Val Pro Asp Arg Phe Ser Gly Ser Gly Ser Gly Thr Asp
        195                 200                 205
Phe Thr Leu Lys Ile Ser Arg Val Glu Ala Glu Asp Val Gly Val Tyr
    210                 215                 220
Tyr Cys Phe Gln Gly Ser His Val Pro Leu Thr Phe Gly Ala Gly Thr
225                 230                 235                 240
Lys Leu Glu Leu Lys Gly Ala Pro Thr Thr Thr Pro Ala Pro Arg Pro
                245                 250                 255
Pro Thr Pro Ala Pro Thr Ile Ala Ser Gln Pro Leu Ser Leu Arg Pro
            260                 265                 270
Glu Ala Cys Arg Pro Ala Ala Gly Gly Ala Val His Thr Arg Gly Leu
```

```
                275                 280                 285
Asp Phe Ala Cys Asp Ile Tyr Ile Trp Ala Pro Leu Ala Gly Thr Cys
290                 295                 300

Gly Val Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
                355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
                450                 455                 460

Met Gln Ala Leu Pro Pro Arg
465                 470

<210> SEQ ID NO 27
<211> LENGTH: 471
<212> TYPE: PRT
<213> ORGANISM: Artificial Sequence
<220> FEATURE:
<223> OTHER INFORMATION: synthesized

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Tyr Met Tyr Trp Val Arg Gln Ala Pro Gly Lys Gly Leu Glu Trp Val
            35                  40                  45

Ala Ser Ile Ser Phe Asp Gly Thr Tyr Thr Tyr Tyr Thr Asp Arg Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Ala Trp Phe Pro Tyr Trp Gly Gln Gly Thr Leu
                100                 105                 110

Val Thr Val Ser Ala Gly Gly Gly Gly Ser Gly Gly Gly Gly Ser Gly
            115                 120                 125

Gly Gly Gly Ser Gly Asp Ile Val Met Thr Gln Thr Pro Leu Ser Leu
            130                 135                 140

Ser Val Thr Pro Gly Gln Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
```

165                 170                 175
Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Leu Thr Phe Gly Ala Gly Thr
225                 230                 235                 240

Lys Leu Glu Leu Lys Gly Ala Pro Thr Thr Thr Pro Ala Pro Arg Pro
            245                 250                 255

Pro Thr Pro Ala Pro Thr Ile Ala Ser Gln Pro Leu Ser Leu Arg Pro
        260                 265                 270

Glu Ala Cys Arg Pro Ala Ala Gly Gly Ala Val His Thr Arg Gly Leu
    275                 280                 285

Asp Phe Ala Cys Asp Ile Tyr Ile Trp Ala Pro Leu Ala Gly Thr Cys
290                 295                 300

Gly Val Leu Leu Leu Ser Leu Val Ile Thr Leu Tyr Cys Arg Ser Lys
305                 310                 315                 320

Arg Ser Arg Gly Gly His Ser Asp Tyr Met Asn Met Thr Pro Arg Arg
            325                 330                 335

Pro Gly Pro Thr Arg Lys His Tyr Gln Pro Tyr Ala Pro Pro Arg Asp
        340                 345                 350

Phe Ala Ala Tyr Arg Ser Arg Val Lys Phe Ser Arg Ser Ala Asp Ala
    355                 360                 365

Pro Ala Tyr Gln Gln Gly Gln Asn Gln Leu Tyr Asn Glu Leu Asn Leu
370                 375                 380

Gly Arg Arg Glu Glu Tyr Asp Val Leu Asp Lys Arg Arg Gly Arg Asp
385                 390                 395                 400

Pro Glu Met Gly Gly Lys Pro Gln Arg Arg Lys Asn Pro Gln Glu Gly
            405                 410                 415

Leu Tyr Asn Glu Leu Gln Lys Asp Lys Met Ala Glu Ala Tyr Ser Glu
        420                 425                 430

Ile Gly Met Lys Gly Glu Arg Arg Arg Gly Lys Gly His Asp Gly Leu
    435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 28
<211> LENGTH: 459
<212> TYPE: PRT
<213> ORGANISM: Artificial Sequence
<220> FEATURE:
<223> OTHER INFORMATION: synthesized

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ser Ile Ser Phe Asp Gly Thr Tyr Thr Tyr Tyr Thr Asp Arg Val

```
                50              55              60
Lys Gly Arg Phe Thr Ile Ser Arg Asp Asn Ser Lys Asn Thr Leu Tyr
 65              70              75              80

Leu Gln Met Asn Ser Leu Arg Ala Glu Asp Thr Ala Val Tyr Tyr Cys
                 85              90              95

Ala Arg Asp Arg Pro Ala Trp Phe Pro Tyr Trp Gly Gln Gly Thr Leu
            100             105             110

Val Thr Val Ser Ala Gly Gly Gly Ser Gly Gly Gly Ser Gly
        115             120             125

Gly Gly Gly Ser Gly Asp Ile Val Met Thr Gln Thr Pro Leu Ser Leu
        130             135             140

Ser Val Thr Pro Gly Gln Pro Ala Ser Ile Ser Cys Arg Ser Ser Gln
145             150             155             160

Ser Ile Val His Ser Asn Gly Asn Thr Tyr Leu Glu Trp Tyr Leu Gln
                165             170             175

Lys Pro Gly Gln Ser Pro Gln Leu Leu Ile Tyr Lys Val Ser Asn Arg
            180             185             190

Phe Ser Gly Val Pro Asp Arg Phe Ser Gly Ser Gly Ser Gly Thr Asp
        195             200             205

Phe Thr Leu Lys Ile Ser Arg Val Glu Ala Glu Asp Val Gly Val Tyr
210             215             220

Tyr Cys Phe Gln Gly Ser His Val Pro Leu Thr Phe Gly Ala Gly Thr
225             230             235             240

Lys Leu Glu Leu Lys Gly Ala Pro Gly Gly Gly Ser Gly Glu Pro Lys
            245             250             255

Ser Ser Asp Lys Thr His Thr Cys Pro Pro Cys Pro Ala Pro Glu Leu
            260             265             270

Leu Gly Gly Pro Asp Phe Trp Val Leu Val Val Gly Gly Val Leu
        275             280             285

Ala Cys Tyr Ser Leu Leu Val Thr Val Ala Phe Ile Ile Phe Trp Val
290             295             300

Lys Arg Gly Arg Lys Lys Leu Leu Tyr Ile Phe Lys Gln Pro Phe Met
305             310             315             320

Arg Pro Val Gln Thr Thr Gln Glu Glu Asp Gly Cys Ser Cys Arg Phe
            325             330             335

Pro Glu Glu Glu Glu Gly Gly Cys Glu Leu Arg Val Lys Phe Ser Arg
        340             345             350

Ser Ala Asp Ala Pro Ala Tyr Gln Gln Gly Gln Asn Gln Leu Tyr Asn
            355             360             365

Glu Leu Asn Leu Gly Arg Arg Glu Glu Tyr Asp Val Leu Asp Lys Arg
370             375             380

Arg Gly Arg Asp Pro Glu Met Gly Gly Lys Pro Gln Arg Arg Lys Asn
385             390             395             400

Pro Gln Glu Gly Leu Tyr Asn Glu Leu Gln Lys Asp Lys Met Ala Glu
            405             410             415

Ala Tyr Ser Glu Ile Gly Met Lys Gly Glu Arg Arg Arg Gly Lys Gly
            420             425             430

His Asp Gly Leu Tyr Gln Gly Leu Ser Thr Ala Thr Lys Asp Thr Tyr
        435             440             445

Asp Ala Leu His Met Gln Ala Leu Pro Pro Arg
450             455

<210> SEQ ID NO 29
```

```
<211> LENGTH: 114
<212> TYPE: PRT
<213> ORGANISM: Artificial Sequence
<220> FEATURE:
<223> OTHER INFORMATION: synthesized

<400> SEQUENCE: 29

Asp Ile Val Leu Thr Gln Thr Thr Leu Ser Leu Asn Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala

<210> SEQ ID NO 30
<211> LENGTH: 118
<212> TYPE: PRT
<213> ORGANISM: Artificial Sequence
<220> FEATURE:
<223> OTHER INFORMATION: synthesized

<400> SEQUENCE: 30

Glu Val Gln Leu Glu Glu Ser Gly Gly Gly Leu Val Lys Pro Gly Gly
1               5                   10                  15

Ser Leu Lys Leu Pro Cys Ala Ala Ser Gly Ser Ser Phe Ser Asp Phe
            20                  25                  30

Tyr Met Tyr Trp Val Arg Gln Thr Pro Glu Lys Arg Leu Glu Trp Val
        35                  40                  45

Ala Ser Ile Ser Phe Asp Gly Thr Tyr Thr Tyr Tyr Thr Asp Arg Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Pro Ala Trp Phe Pro Tyr Trp Gly Gln Gly Thr Leu
            100                 105                 110

Val Thr Val Ser Ala Ala
            115
```

CADHERIN-17 SPECIFIC ANTIBODIES AND CYTOTOXIC CELLS FOR CANCER TREATMENT

CROSS REFERENCE TO RELATED PATENT APPLICATIONS

This application claims priority over U.S. Provisional Application No. 62/276,855, filed Jan. 9, 2016, titled "Cadherin-17 specific antibodies and cytotoxic cells for cancer treatment," which is hereby incorporated by reference in its entirety.

TECHNICAL FIELD

The present disclosure generally relates to the technical field of cancer immunotherapy, and more particularly to cadherin-17 specific antibodies and cytotoxic cells for cancer treatment.

BACKGROUND

Despite the recent advances in drug discovery and clinical imaging, cancer remains one of the deadliest diseases in humans. Our understandings on how tumor initiates, survives under stress, colonizes/metastasizes to distant organs and sites, and becomes resistant to drugs are still limited. The American Cancer Society estimated new cases of cancer in the U.S. in 2014 is 1.6 million, with no approved curative treatment for most of the predominant types of cancer. In China, cancers are among the top killers with increasing incidences and death rates, which are believed attributable to the viral/bacterial endemic (Hepatitis B virus [HBV] and *Helicobacter pylori* infections), environmental pollutions and food contaminations.

Stomach and liver cancers are among the most lethal of malignancies worldwide and over half of the incidences diagnosed in China, causing >1.42 million deaths per year globally, yet there is no effective therapy. New biomarkers and therapeutic targets are thus needed for potential drug development against these aggressive cancers, in particular for those in advanced stages. A proven molecular targeting agent that can eliminate or repress the growth of these two cancers will have important clinical values and significant market impact. These tumors can be resected effectively by surgery if the diseases are diagnosed in early stages. Unfortunately, and very often, most of these cancers are asymptomatic and detected at very advanced stages when presented in the clinic. Without effective treatment, these patients die shortly after the diagnosis or relapse after salvage therapies.

CART-cell treatments are a kind of adoptive cell therapy that comprises the ex vivo modification of T cells to direct an anti-cancer response. CAR-modified T cells can be engineered to target virtually any tumor associated antigen.

Almost all the early-stage CART studies focus on blood cancers including the proof-of-concept study of CART19 (CAR-T cells targeting CD19 antigen) in pediatric acute lymphoblastic leukemia. It remains to be seen whether CAR-T cell therapies and related technologies can repeat the same efficacy in solid tumor indications, such as liver, stomach and lung cancers. Currently, there is a total of 72 clinical trials registered at www.clinicaltrials.gov and 15 studies enrolled in China. Over half of the studies focus on blood cancers with CD19 the most common CAR-T target, followed by GD2 and Her2 specific for a brain tumor and an array of Her2-positive cancers. Thus, there is a huge gap on CAR-T immunotherapy for HCC and GC.

Today, there is only one registered CAR-T phase 1 trial for treating patients with advanced HCC using, KJgpc3-001, a genetically modified T cell which expresses a third-generation GPC3-targeted CAR. GPC3 (glypican-3) is highly expressed in HCC but the limited expression in normal tissues (63.6% vs. 9.2%). Unfortunately, no partial or complete response was observed in the phase I study of anti-GPC3 mAb GC33 (developed by Chugai, a subsidiary of Roche). KJgpc3-001 comprises anti-GPC3 scFv derived from GC33 and an intracellular signaling domain derived from CD28/4-1BB/CDζ. KJgpc3-001 could be transduced into patient's T cells with the lentiviral vector to attack the liver cancer. In preclinical studies, all mice treated with KJgpc3-001 survived for longer than 60 days, while the median survival of the saline-treated mice was 33 days. A major concern about KJgpc3-001 is the expression of GPC3 in normal tissues such as gastric glands, kidney tubules, and germ cells. Previously, one patient with breast cancer died after the treatment with HER2-targeted CAR due to the expression of HER2 in lung tissues. The patient experienced respiratory distress within 15 minutes after cell infusion and died 5 days after treatment. Therefore, there is a need for cancer immunotherapy using cadherin-17 specific antibodies and cytotoxic cells for cancer treatment.

SUMMARY

The disclosure provides cadherin-17 specific antibodies and cytotoxic cells.

Embodiments of the present disclosure relate to an antibody having specificity for cadherin-17, comprising an amino acid sequence having at least 70% similarity with an amino acid sequence selected from SEQ ID NO: 1-21.

In some embodiments, the antibody may include an amino acid sequence having at least 80% similarity with an amino acid sequence selected from SEQ ID NO: 1-21.

In some embodiments, the antibody may include an amino acid sequence having at least 95% similarity with an amino acid sequence selected from SEQ ID NO. 1-21.

In some embodiments, the monoclonal antibody is a mouse antibody, a humanized antibody, or a human antibody. In some embodiments, the monoclonal antibody is a human antibody isolated from a phage library screen.

In some embodiments, the antibody may include a variable region of light chain (VL), a variable region of heavy chain (VH), and the VL may include an amino acid sequence having at least 90% similarity with an amino acid sequence selected from SEQ ID NO: 1, 3, 6, 8, 10, 12, 14, and 16. In some embodiments, the VH may include an amino acid sequence having at least 90% similarity with an amino acid sequence selected from SEQ ID NO: 2, 4, 5, 7, 9, 11, 13, and 15.

In some embodiments, the antibody may include a conjugated cytotoxic moiety. In some embodiments, the conjugated cytotoxic moiety may include irinotecan, auristatins, PBDs, maytansines, amantins, spliceosome inhibitors, or a combination thereof. In some embodiments, the conjugated cytotoxic moiety may include a chemotherapeutic agent.

In some embodiments, the antibody is a bispecific antibody.

In some embodiments, the antibody may include specificity for a cell receptor from a cytotoxic T or NK cell. In some embodiments, the antibody is a bispecific antibody having specificity for both cadherin-17 and CD3. In some embodiments, the cell receptor may include 4-1BB, OX40, CD27, CD40, TIM-1, CD28, HVEM, GITR, ICOS, IL12receptor, IL14 receptor, or a derivative or combination thereof.

In some embodiments, the antibody may include a first single-chain variable fragment (ScFv) having specificity for cadherin-17 and a second sing-chain variable fragment (ScFv) having specificity for CD3, wherein the first ScFv may include a first VH and a first VL, the second ScFv may include a second VH and a second VL. In some embodiments, the first VH may include an amino acid sequence selected from SEQ ID NO: 2, 4, 5, 7, 9, 11, 13, and 15. In some embodiments, the first VL may include an amino acid sequence selected from SEQ ID NO: 1, 3, 6, 8, 10, 12, 14, and 16.

In some embodiments, the second VH may include a corresponding portion of an amino acid sequence of SEQ ID NO: 18.

In some embodiments, the second VL may include a corresponding portion of an amino acid sequence of SEQ ID NO: 18.

In some embodiments, the antibody may include specificity for an immune checkpoint inhibitor. In some embodiments, the checkpoint inhibitor may include PD-1, TIM-3, LAG-3, TIGIT, CTLA-4, PD-L1, BTLA, VISTA, or a combination thereof.

In some embodiments, the antibody may include specificity for an angiogenic factor. In some embodiments, the angiogenic factor may include VEGF.

In some embodiments, the antibody is configured to antagonize the binding of the RGD site in cadherin-17 domain 6 to integrin. In some embodiments, the integrin may include alpha2beta1.

In some embodiments, the antibody is a monoclonal antibody.

Some embodiments of the present disclosure relate to an IgG heavy chain for an antibody, comprising an amino acid sequence having a sequence selected from SEQ ID NO: 2, 4, 5, 7, 9, 11, 13, and 15.

Some embodiments of the present disclosure relate to a light chain for an antibody, comprising an amino acid sequence having a sequence selected from SEQ ID NO: 1, 3, 6, 8, 10, 12, 14, and 16.

Some embodiments of the present disclosure relate to a variable chain for an antibody, comprising an amino acid sequence selected from SEQ ID NO: 1-16.

Some embodiments of the present disclosure relate to a scFv or Fab having specificity for cadherin-17, comprising an amino acid sequence having at least 90% similarity with an amino acid sequence selected from SEQ ID NO: 1-21.

In some embodiments, the scFv or Fab may include specificity for a cell receptor from a cytotoxic T or NK cell. In some embodiments, the scFv or Fab may include specificity for an immune checkpoint inhibitor. In some embodiments, the scFv or Fab may include specificity for an angiogenic factor.

Some embodiments of the present disclosure relate to a T or NK cell having specificity for cadherin-17, wherein the T or NK cell may include a chimeric antigen receptor, wherein the chimeric antigen receptor may include an amino acid sequence having at least 90% similarity with an amino acid sequence selected from SEQ ID NO: 1-21.

In some embodiments, the chimeric antigen receptor may include an amino acid sequence selected from SEQ ID NO: 1-16.

Some embodiments of the present disclosure relate to an isolated nucleic acid encoding the antibody, the IgG heavy Chain, the light chain, the variable chain, or the ScFv or Fab as described above.

Some embodiments of the present disclosure relate to an expression vector comprising the isolated nucleic acid of those described above. In some embodiments, the vector is expressible in a cell.

Some embodiments of the present disclosure relate to a host cell comprising the nucleic acid as described above.

Some embodiments of the present disclosure relate to a host cell comprising the expression vector as described above.

In some embodiments, the host cell is a prokaryotic cell or a eukaryotic cell.

Some embodiments of the present disclosure relate to a pharmaceutical composition, comprising the antibody of Claim 1-26 and a cytotoxic agent.

In some embodiments, the cytotoxic agent may include cisplatin, gemcitabine, irinotecan, or an anti-tumor antibody.

In some embodiments, the pharmaceutical composition may include the antibody as described above and a pharmaceutically acceptable carrier.

Some embodiments of the present disclosure relate to a method for treating a subject having cancer, comprising administering to the subject an effective amount of the antibody of Claim 1-26 or the T or NK cell of Claims 34-35.

In some embodiments, the cancer is liver cancer, gastric cancer, colon cancer, pancreatic cancer, lung cancer, or a combination thereof.

The objectives and advantages of the disclosure may become apparent from the following detailed description of preferred embodiments thereof in connection with the accompanying drawings.

BRIEF DESCRIPTION OF THE DRAWINGS

Preferred embodiments according to the present disclosure may now be described with reference to the FIGS, in which like reference numerals denote like elements.

FIG. 1 shows murine VL and VH sequences of Lic3 and Lic5 (Please note that Lic3 sequences have been updated, i.e. SEQ ID NO. 1 and SEQ ID NO. 2 in prf need to be replaced accordingly).

FIG. 2 shows a homology of Lic3 VL sequence to human VL 2-30/J1 for humanization and humanized variants that are indicated by Hum, where dots indicate the human amino acid and back mutations are indicated by the single amino acid annotation.

FIG. 3 shows a homology of Lic3 VL sequence to human VL 2-24/J1 and Lic3 Vk sequence to human VH Vk2-29 for humanization and humanized variants that are indicated by Hum, where dots indicate the human amino acid and back mutations are indicated by the single amino acid annotation.

Figure 4:
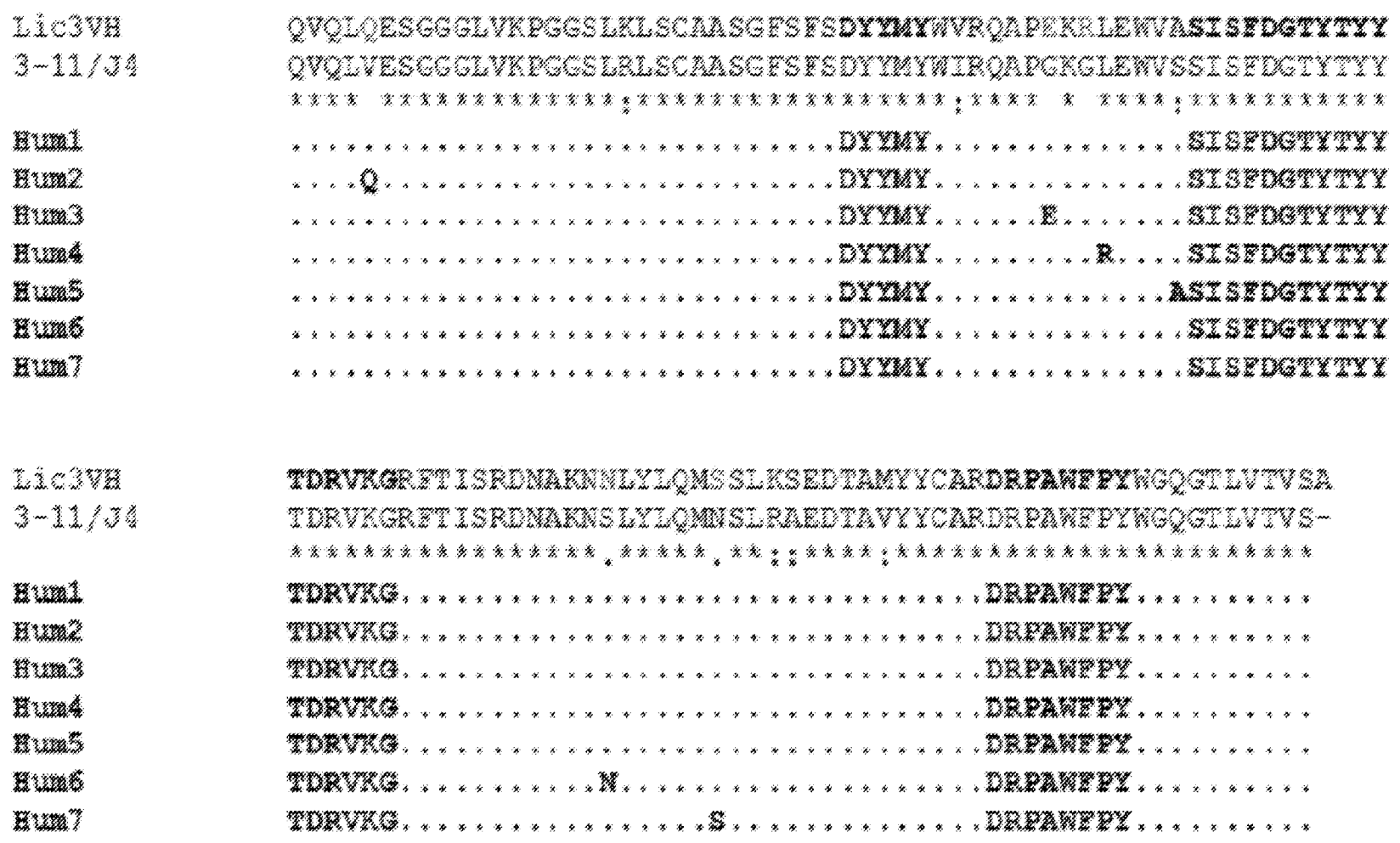

FIG. 4 shows a homology of Lic3 VH sequence to human VH 3-11/J4 for humanization and humanized variants that are indicated by Hum, where dots indicate the human amino acid, and back mutations are indicated by the single amino acid annotation.

FIG. 5 shows a homology of Lic3 VH sequence to human VH 3-30/J4 for humanization and humanized variants that are indicated by Hum, where dots indicate the human amino acid, and back mutations are indicated by the single amino acid annotation.

FIG. 6 shows a homology of Lic5 VL sequence to human VL IGKV 2-30 for humanization and humanized variants that are indicated by Hum, where dots indicate the human amino acid, and back mutations are indicated by the single amino acid annotation.

FIG. 7 shows a homology of Lic5 VL sequence to human VL pdb4X0K for humanization and humanized variants that are indicated by Hum, where dots indicate the human amino acid and back mutations are indicated by the single amino acid annotation.

FIG. 8 shows a homology of Lic5 VH sequence to human VH IGHV3-21 for humanization and humanized variants that are indicated by Hum, where dots indicate the human amino acid, and back mutations are indicated by the single amino acid annotation.

Figure 9:
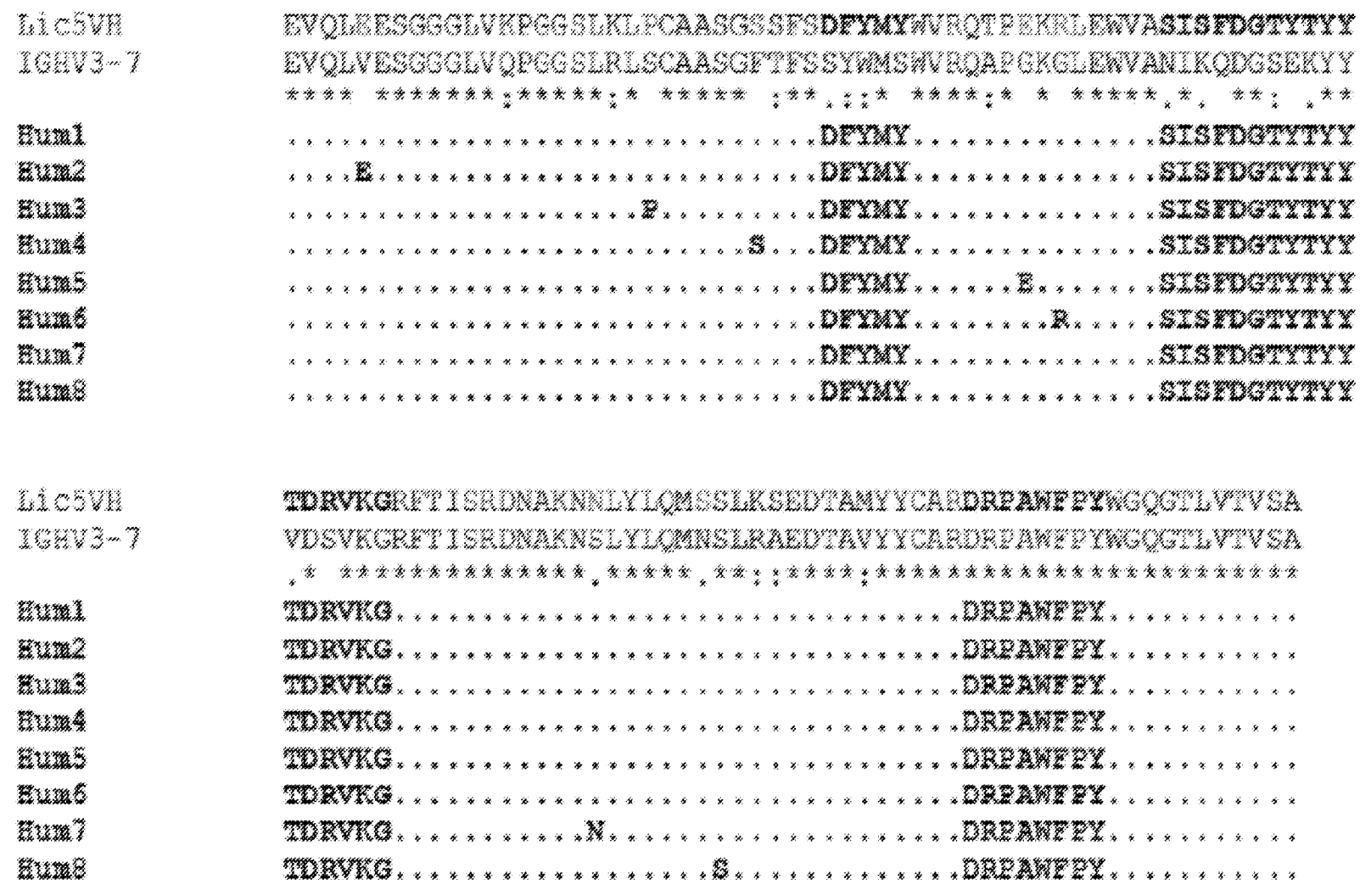

FIG. 9 shows a homology of Lic5 VH sequence to human VH IGHV3-7 for humanization and humanized variants that are indicated by Hum, where dots indicate the human amino acid, and back mutations are indicated by the single amino acid annotation.

FIG. 12 shows human CDH17antibody VL and VH sequences from phage library screen.

FIG. 14 shows the amino acid sequences of an exemplary CDH17-CD3 bispecific antibody (Knob in hole).

FIG. 19 presents the binding of humanized Lic3 to CDH17 as determined by ELISA.

FIG. 24 shows an amino acid sequence (SEQ ID NO. 19) of Lic3 $2^{nd}$ generation CAR (Lic3scFv-CD28hinge+TM+endo-CD3zeta endo).

FIG. 25 shows an amino acid sequence (SEQ ID NO. 20) of Lic5 $2^{nd}$ generation CAR (Lic5scFv-CD28hinge+TM+endo-CD3zeta endo).

FIG. 26 shows an amino acid sequence (SEQ ID NO. 21) of HLic26 $2^{nd}$ generation CAR (Lic26scFv-CD28hinge+TM+endo-CD3zeta endo).

FIG. 27 shows an amino acid sequence (SEQ ID NO. 22) of Lic3 $3^{rd}$ generation CAR (Lic3scFv-CD28-4-1BB-CD3zeta endo).

FIG. 28 shows an amino acid sequence (SEQ ID NO. 23) of Lic5 $3^{rd}$ generation CAR (Lic5scFv-CD28hinge+TM+endo-4-1BB endo-CD3zeta endo).

FIG. 29 shows an amino acid sequence (SEQ ID NO. 24) of HuLic26 $3^{rd}$ generation CAR (Lic26scFv-CD28hinge+TM+endo-4-1BB endo-CD3zeta endo).

DETAILED DESCRIPTION

Figure 10:
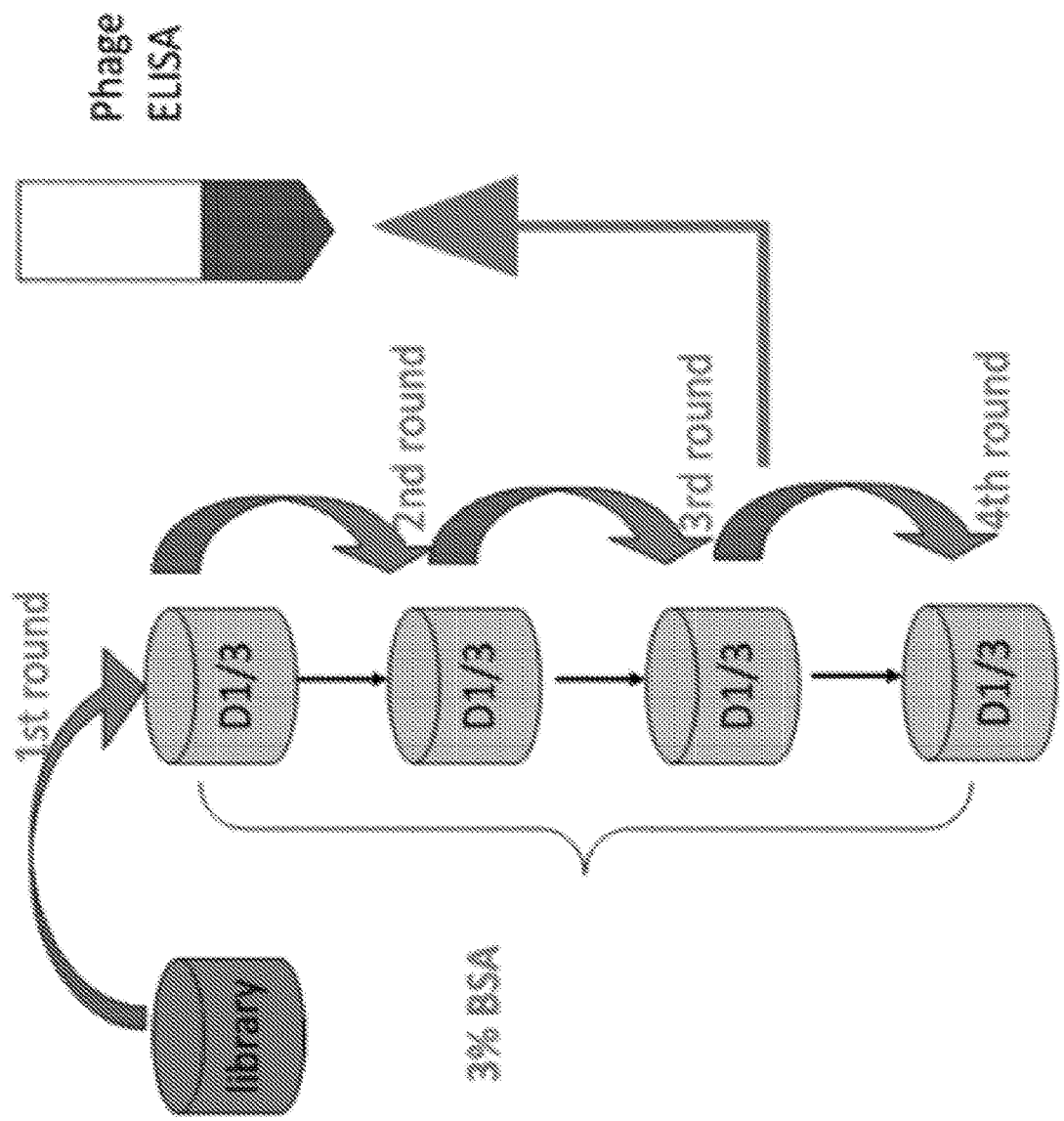
FIG. 10 shows a flowchart illustrating the process of isolating human cadherin-17 specific antibodies from an antibody phage library, where human cadherin-17 specific antibodies were isolated from a phage library by multiple rounds of binding to immobilized CDH17 domains 1-3.

The applications provide antibodies specific for cadherin-17 (CDH17), antibodies targeting tumor cells and anti-tumor immunotherapies using such antibodies. Such immunotherapies include antibodies possessing different modes of cytotoxicity or chimeric antigen receptors that stimulate T or NK cell cytotoxicity.

Unless defined otherwise, all technical and scientific terms used herein have the same meaning as commonly understood by those of ordinary skill in the art to which the present disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T" is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

As used herein, the terms "function" and "functional" and the like refer to a biological, binding, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, Nucleic Acids Research 12, 387-395) which is incorporated herein by reference. In this way, sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the present disclosure. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the present disclosure. A host cell which comprises a recombinant vector of the present disclosure is a recombinant host cell.

An "isolated" antibody is one which has been identified and separated and/or recovered from a component of its natural environment. Contaminant components of its natural environment are materials which would interfere with diagnostic or therapeutic uses for the antibody and may include enzymes, hormones, and other proteinaceous or non proteinaceous solutes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules, therefore, are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA and RNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard; it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "reference sequence" generally refers to a nucleic acid coding sequence, or amino acid sequence, to which another sequence is being compared. All polypeptide and polynucleotide sequences described herein are included as references sequences.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95%, 96%, 97%, 98%, 99% or greater of some given quantity.

"Treating" or "treatment" or "alleviation" refers to both therapeutic treatment and prophylactic or preventative measures, wherein the object is to prevent or slow down (lessen) the targeted pathologic condition or disorder. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In a preferred embodiment, the cancer patients are still progression-free in cancer after one year, preferably after 15 months. These parameters for assessing successful treatment and improvement in the disease are readily measurable by routine procedures familiar to a physician of appropriate skill in the art.

The terms "modulating" and "altering" include "increasing" and "enhancing" as well as "decreasing" or "reducing," typically in a statistically significant or a physiologically significant amount or degree relative to a control. In specific embodiments, immunological rejection associated with transplantation of the blood substitutes is decreased relative to an unmodified or differently modified stem cell by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

An "increased" or "enhanced" amount is typically a "statistically significant" amount, and may include an increase that is 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By "obtained from" is meant that a sample such as, for example, a polynucleotide or polypeptide is isolated from, or derived from, a particular source, such as the desired organism or a specific tissue within the desired organism. "Obtained from" can also refer to the situation in which a polynucleotide or polypeptide sequence is isolated from, or derived from, a particular organism or tissue within an organism. For example, a polynucleotide sequence encoding a reference polypeptide described herein may be isolated from a variety of prokaryotic or eukaryotic organisms, or from particular tissues or cells within a certain eukaryotic organism. A "therapeutically effective amount" refers to an amount of an antibody or a drug effective to "treat" a disease or disorder in a subject. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating."

"Chronic" administration refers to administration of the agent(s) in a continuous mode as opposed to an acute mode, so as to maintain the initial therapeutic effect (activity) for an extended period of time. "Intermittent" administration is a treatment that is not consecutively done without interruption, but rather is cyclic in nature.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the present disclosure, in bacterial or eukaryotic cells. Suitable vectors are disclosed below.

The term "antibody" is used in the broadest sense and specifically covers monoclonal antibodies (including full-length monoclonal antibodies), multispecific antibodies (e.g., bispecific antibodies), and antibody fragments so long as they exhibit the desired biological activity or function.

"Antibody fragments" comprise a portion of a full-length antibody, generally the antigen-binding or variable region of the antibody. Examples of antibody fragments include Fab, Fab', F(ab')2, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of a Fv comprising only three complementarity determining regions (CDRs) specific for an antigen) has the ability to recognize and bind antigen, although at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring the production of the antibody by any particular method. For example, the monoclonal antibodies to be used in accordance with the present disclosure may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The term "variable" refers to the fact that certain segments of the variable domains (V domains) differ extensively in sequence among antibodies. The V domain mediates antigen binding and defines the specificity of a particular antibody for its particular antigen. However, the variability is not evenly distributed across the 10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four frameworks regions (FRs), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen but exhibit various effector functions, such as participation of the antibody in antibody-dependent cellular cytotoxicity (ADCC).

The term "hypervariable region" when used herein refers to the amino acid residues of an antibody which are responsible for antigen-binding. The hypervariable region generally comprises amino acid residues from a CDR (e.g. around about residues 24-34 (L1), 50-56 (L2) and 89-97 (L3) in the VL, and around about 31-35B (H1), 50-65 (H2) and 95-102 (H3) in the VH (Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the VL, and 26-32 (H1), 52A-55 (H2) and 96-101 (H3) in the VH (Chothia and Lesk J. Mol. Biol. 196:901-917 (1987)).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. Proc. Natl Acad. Sci. USA 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. In some embodiments, humanized antibodies are human immunoglobulins (recipient or acceptor antibody) in which hypervariable region residues of the recipient are replaced by hypervariable region residues from a non-human species (donor antibody) such as a mouse, rat, rabbit or nonhuman primate having the desired specificity, affinity, and capacity. In some embodiments, humanized antibodies are antibodies derived from human cells or from transgenic animals (typically mice) with express human antibody genes.

In one aspect, provided herein are antibodies or antigen-binding fragments thereof having specificity for CDH-17. Tumor-associated antigens may serve as targets for anti-tumor immunotherapies by inhibiting their tumor growth promoting activities and by directing cytotoxic activity to tumor cells. Cadherin-17 is a Class 1 plasma membrane glycoprotein that belongs to the cadherin superfamily of cell adhesion molecules. It is a non-classical cadherin possessing 7 cadherin or cadherin-like repeats in its ectodomain. Cadherin-17 (CDH-17) is a tumor-associated antigen that participates in tumor growth. CDH-17 expression normally restricted to intestinal epithelial cells of colon, small intestine, and pancreatic ducts are over-expressed in several tumors types including colon adenocarcinoma, gastric adenocarcinoma, hepatocellular carcinoma and pancreatic adenocarcinoma. Tumor growth promoting activity may involve binding between the RGD motif in CDH17 domain 6 and integrins such as $\alpha_2\beta_1$. An abnormal increase in CDH-17 level in blood and in exosomes may serve as prognostic cancer markers.

Using proteomics and oncogenomics approaches, a therapeutic target, liver-intestine cadherin or cadherin-17 (CDH17) is herein disclosed. The target is overexpressed in a majority of gastric carcinoma (GC) and hepatocellular carcinoma as well as in (HCC) pancreas cancer, colon cancer, ovary cancer and lung cancers. RNAi silencing of CDH17 gene could inhibit tumor growth and metastatic spread in the established HCC mouse models (both xenograft and orthotopic). The underlying antitumor mechanism is based on inactivation of Wnt signaling in concomitance with tumor suppressor pathway reactivation.

The anti-CDH17 antibodies present in this application have shown antitumor effects in multiple in vitro and in vivo systems of liver cancer and stomach cancers. Such antibodies have in vitro and in vivo purification, detection, diagnostic and therapeutic uses. Such antibodies may be developed to support anti-tumor activity by binding selectively to tumor cells and stimulate complement fixation, antibody-dependent cytotoxicity, cytotoxicity mediated by a conjugated drug, lymphocyte mediated cytotoxicity and NK-mediated cytotoxicity. Provided herein are antibodies and humanized antibodies, antigen-binding fragments or chimeric antibody proteins, comprising a heavy chain variable region having an amino acid sequence set forth as a corresponding SEQ ID provided below.

Figure 11:
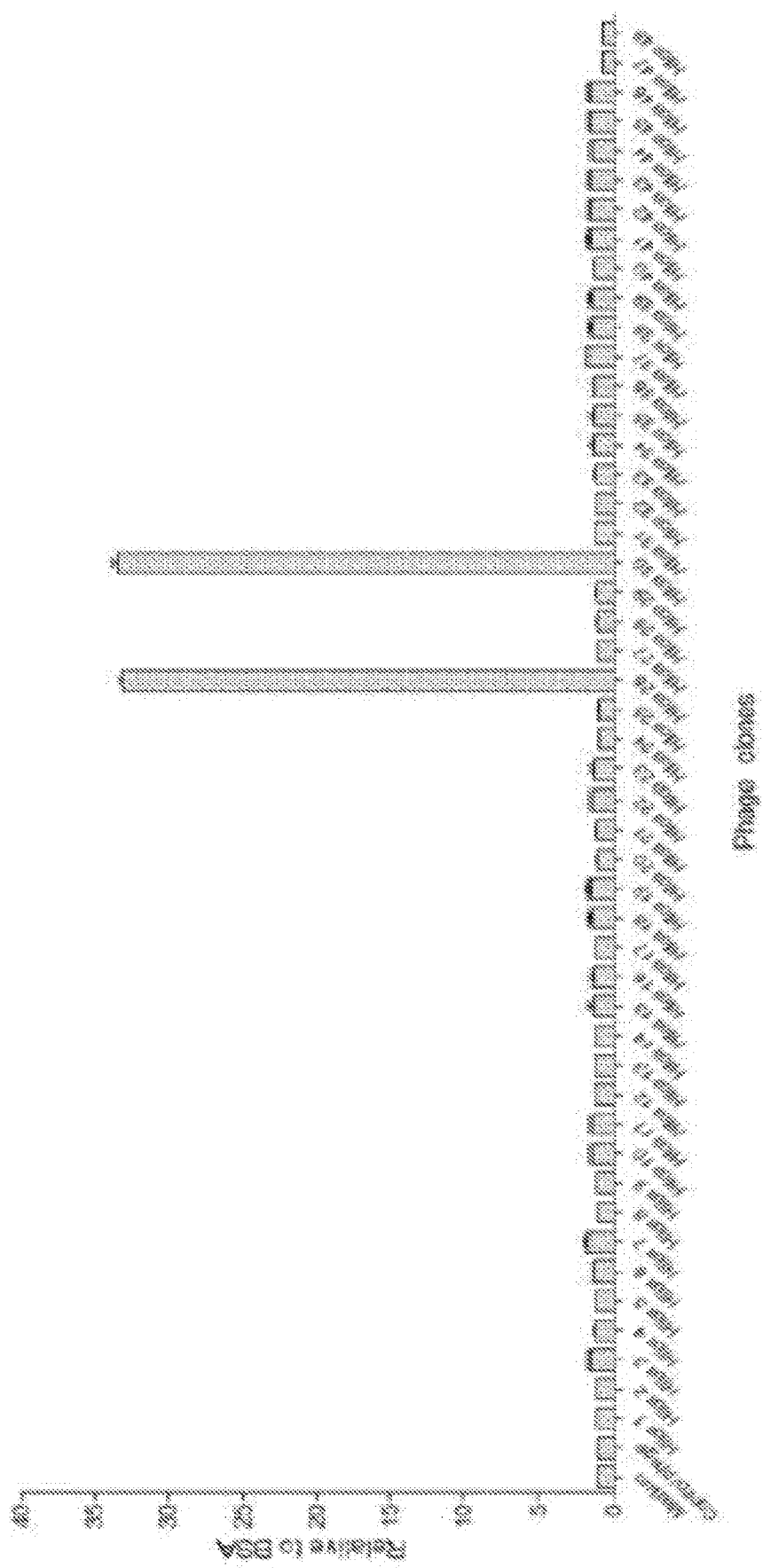
FIG. 11 is a graph showing examples of human antibodies isolated from the antibody phage library binding to CDH17.
Figure 13:
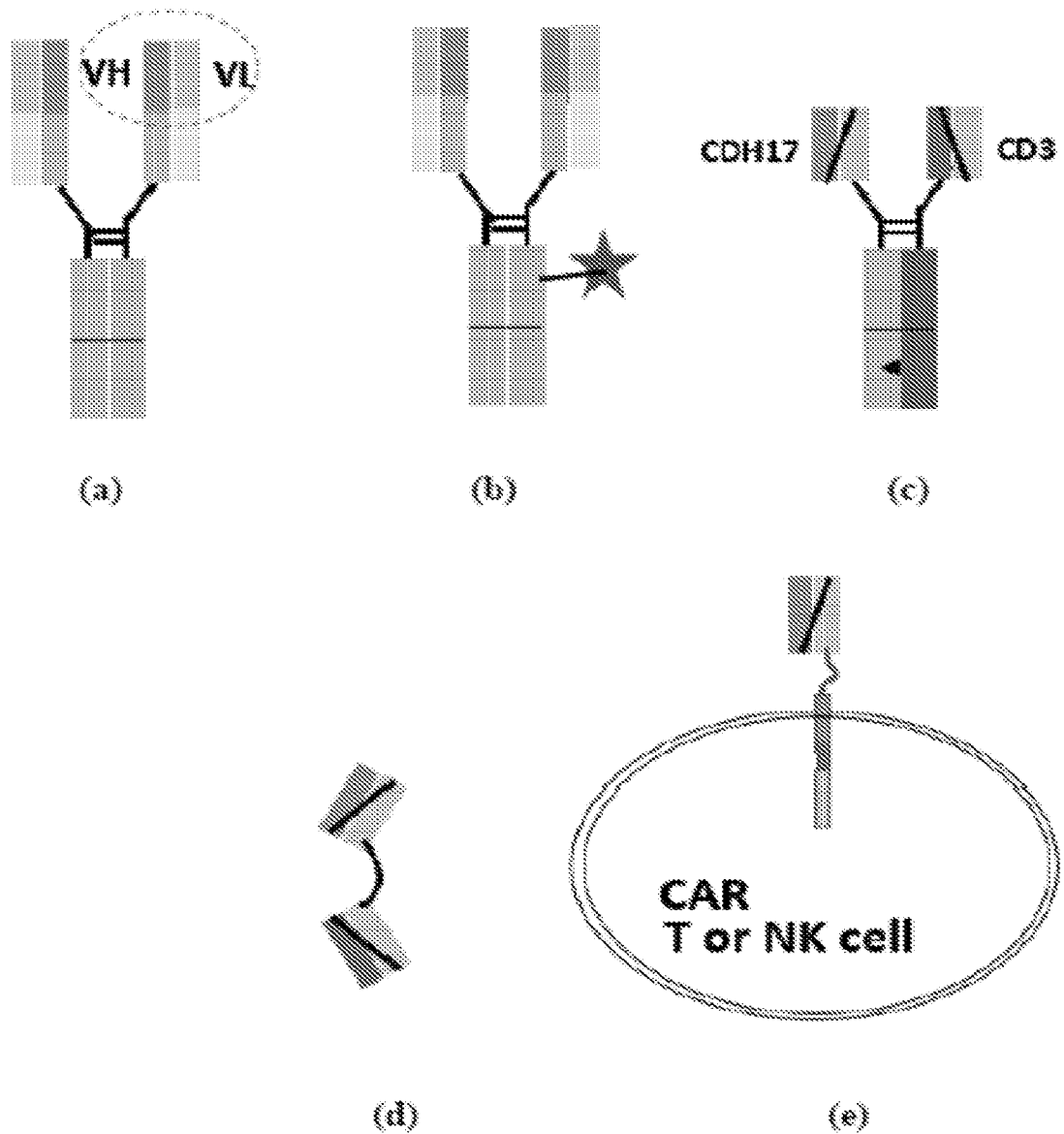
FIG. 13 shows a panel of exemplary functional domain configurations for cancer immunotherapeutics generated from CDH17 antibody VH and VL; (a) CDH17 specific antibody; (b) CDH17 antibody drug conjugate; (c) scFv-Fc bispecific antibody (knob in hole); (d) scFv-Fc bispecific antibody (bite); and (e) CART or NK cell.

CDH17 antibody sequences may include various type of antibodies such as mouse antibodies (Lic3 and Lic5; FIG. 1) and their humanized variants (FIGS. 2-9), human antibodies isolated from a phage library screen (FIGS. 10-12), monospecific antibodies with isotypes to support ADCC, complement fixation, and drug conjugates for cytotoxic anti-cancer activity (preferred conjugate moieties being irinotecan, auristatins, PBDs, maytansines, amantins, spliceosome inhibitors and other chemotherapeutic agents) (FIG. 13), bispecific antibodies, including various engineered antibody fragments (Fab, scFv, diabodies etc). Preferred forms include knobs-into holes and "Bite" (Example sequence in FIG. 14).

Figure 15:
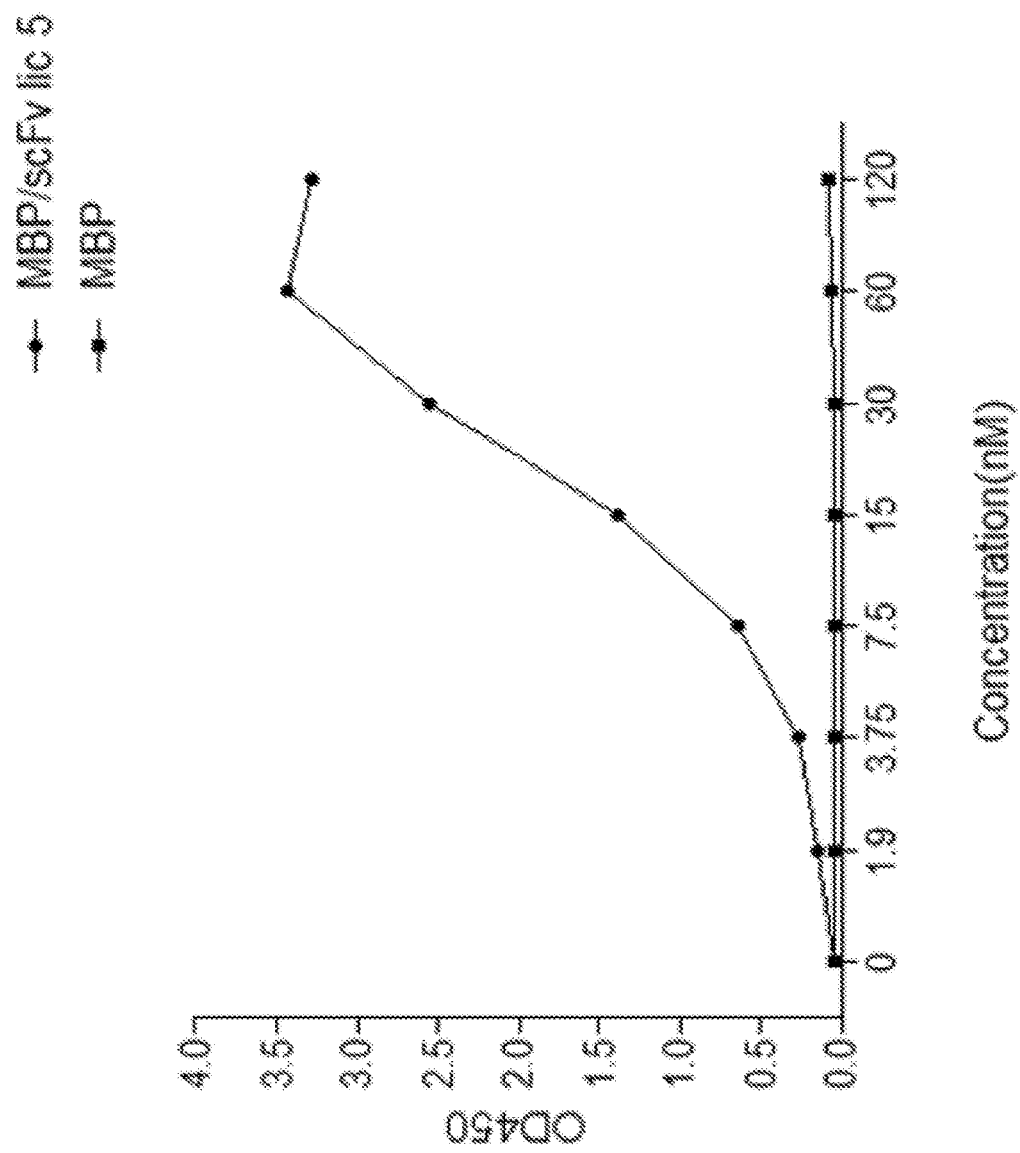
FIG. 15 is a graph showing binding of Lic5 scFv to CDH17 by ELISA.
Figure 16:
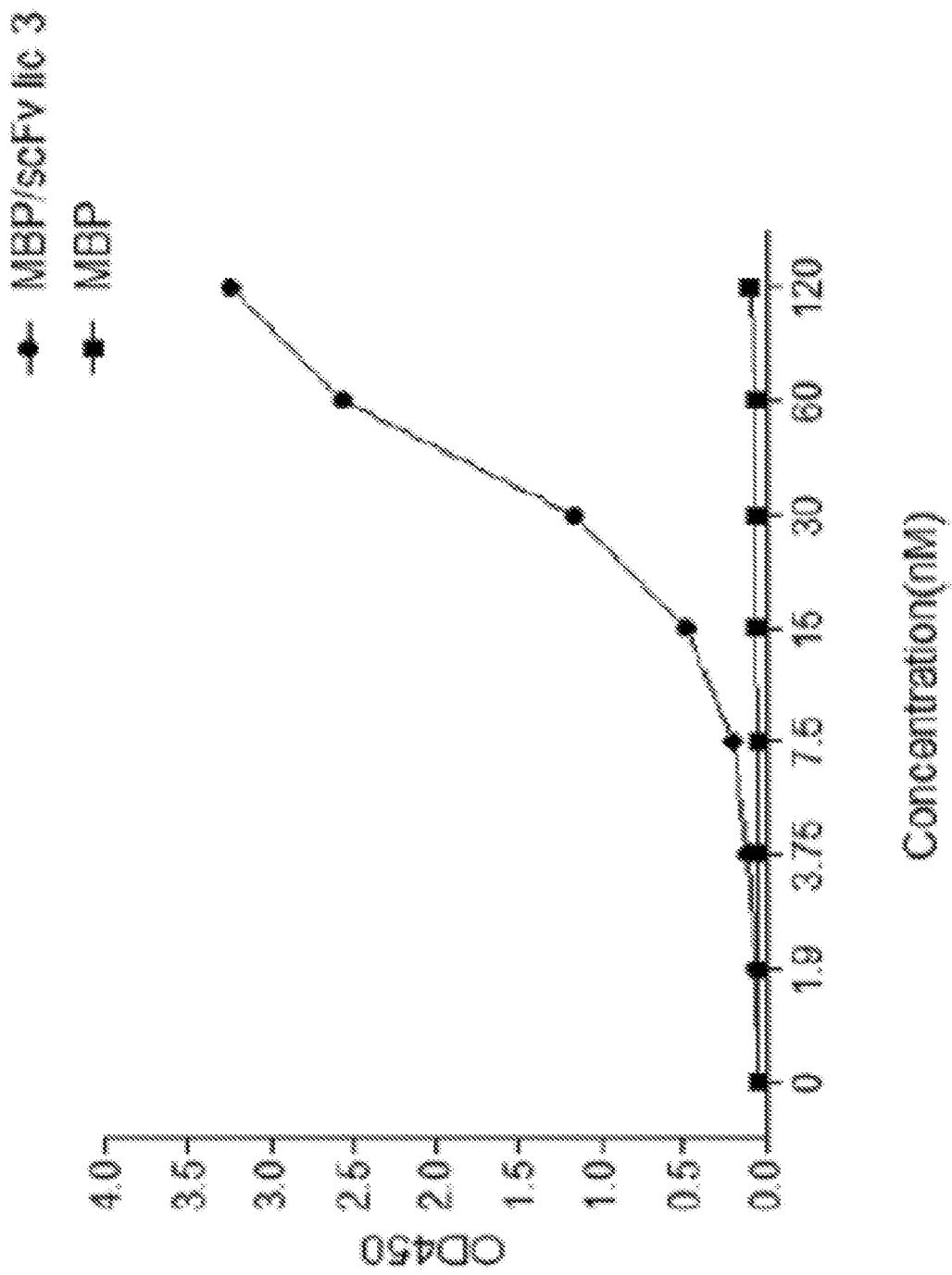
FIG. 16 is a graph showing binding of Lic3 scFv to CDH17 by ELISA.
Figure 17:
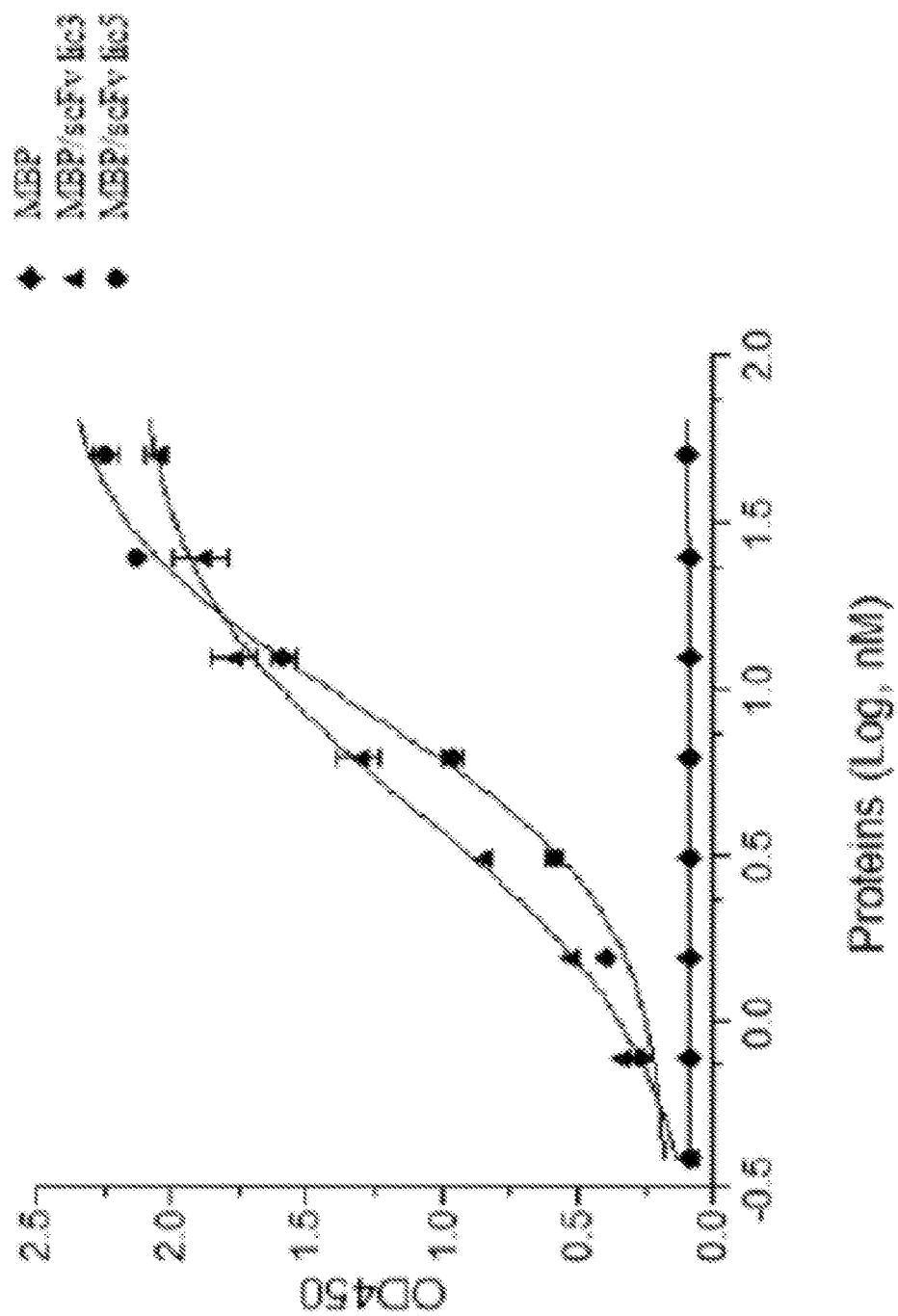
FIG. 17 is a graph showing affinity of Lic3 and Lic5 scFv as determined by ELISA, where scFv lic 3 (kd): 11.88 nM, and scFv lic5: 22.06 nM.

In some embodiments, mouse CDH17 antibodies, Lic5 scFv and Lic3 scFv, display their ability to bind CDH17 in an ELISA assay, respectively (FIGS. 15-16). The binding affinity of Lic3 and Lic5 scFv can also be determined by ELISA, where the Kd of scFv lic 3 and scFv lic5 were 11.88 nM and 22.06 nM, respectively (FIG. 17).

Figure 18:
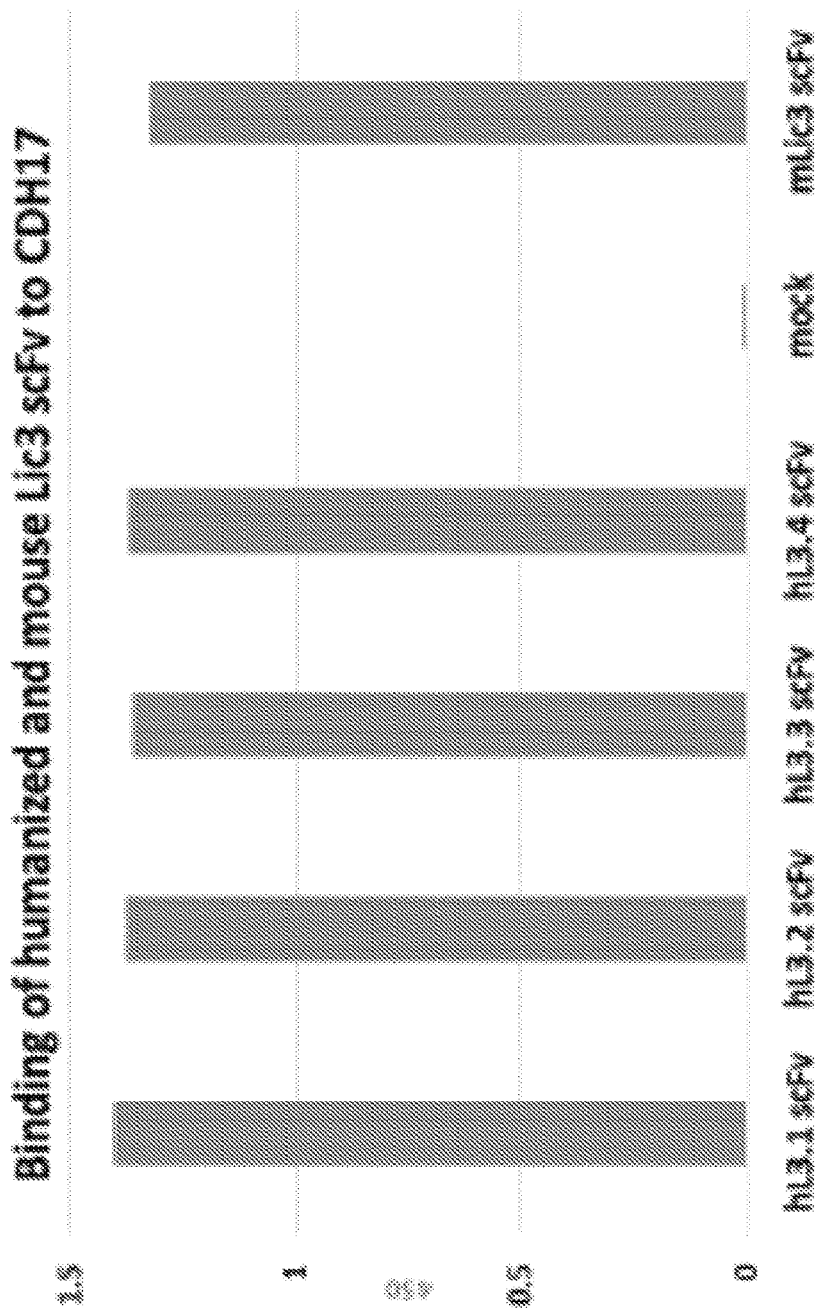
FIG. 18 presents photographs showing the internalization of Lic5 into human gastric cancer cells as candidate for antibody drug conjugate; (a) photographs showing the staining of DAPI (blue) and Lic5-FITC (green) at indicated times; (b) photographs showing the merged staining of DAPI (blue) and Lic5-FITC (green) at indicated times; Lic5-FITC (green) internalization in Oum1 human gastric cancer cells over 30 mins at 37° C. was determined by confocal microscopy; nucleus was stained with DAPI.

In another aspect, the internalization of Lic5 into human gastric cancer cells is indicative of a candidate for antibody drug conjugate as shown in FIG. 18; (a) photographs showing the staining of DAPI (blue) and Lic5-FITC (green) at indicated times; (b) photographs showing the merged staining of DAPI (blue) and Lic5-FITC (green) at indicated times; Lic5-FITC (green) internalization in Oum1 human gastric cancer cells over 30 mins at 37° C. was determined by confocal microscopy; nucleus was stained with DAPI.

In some embodiments, over 200 CDH17 monoclonal antibodies were generated by standard hybridoma technology. Humanized Lic3scFvFc was expressed from CHO cells transfected with four cDNA expression construct clones (hL3.1-3.4). Culture media from transfected or mock transfected CHO was added to a 96-well plate coated with CDH17Fc. Binding was determined using anti-mouse Fc HRP conjugate. Binding was compared to that of a mouse Lic3 scFvFc (mLic3 scFv) also produced in CHO cells (FIG. 19).

Figure 20:
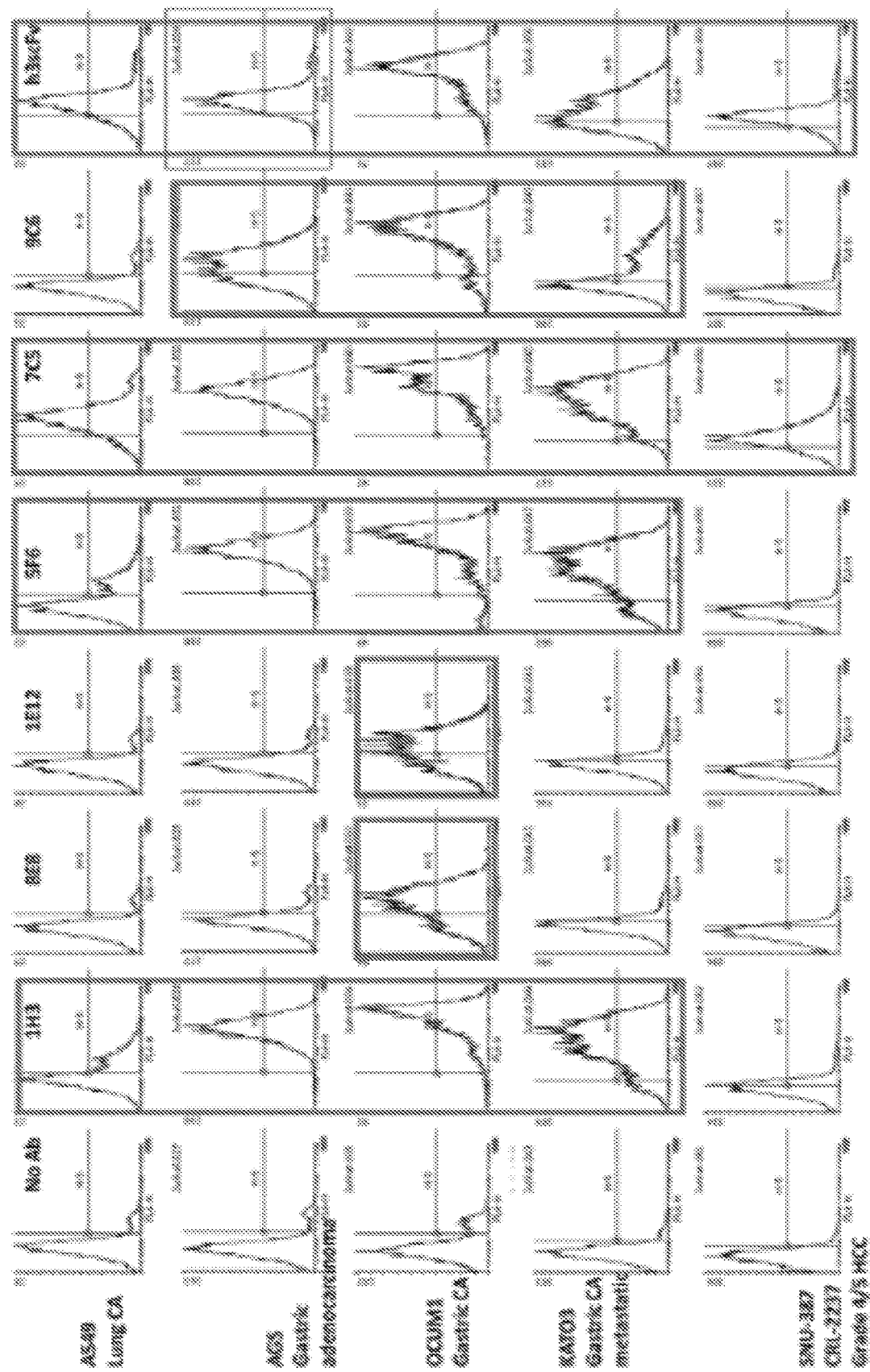
FIG. 20 presents examples of CDH17 monoclonal antibodies binding to CDH17 or CDH17 truncates as determined by ELISA.

In one aspect, mice were immunized with recombinant CDH17 possessing the entire ectodomain of 7 cadherin repeats (D1-7) fused to a modified human IgG4 Fc (CDH17Fc). Hybridoma culture media were a screen for binding to CDH17Fc and lack of binding to IgG4 Fc. CDH17Fc truncates possessing D1, D1-2, D1-3, D3-4, D6 and D5-7 were generated by standard PCR methodology. CDH17 antibodies were identified that bound specifically to each truncate and examples are presented in FIG. 20. A panel of 13 novel CDH17 monoclonal antibodies was analyzed by ELISA for binding to CDH17 possessing all 7 ectodomains or truncates possessing domains 1-2, domains 3-4, domains 5-6 or domain 6. Antibody epitopes were localized to different domains. Surprisingly the binding of certain antibodies was found to be restricted to CDH17 produced in CHO cells whereas the binding of other antibodies was found to be restricted to CDH17 produced in 293 F cells.

Figure 21:
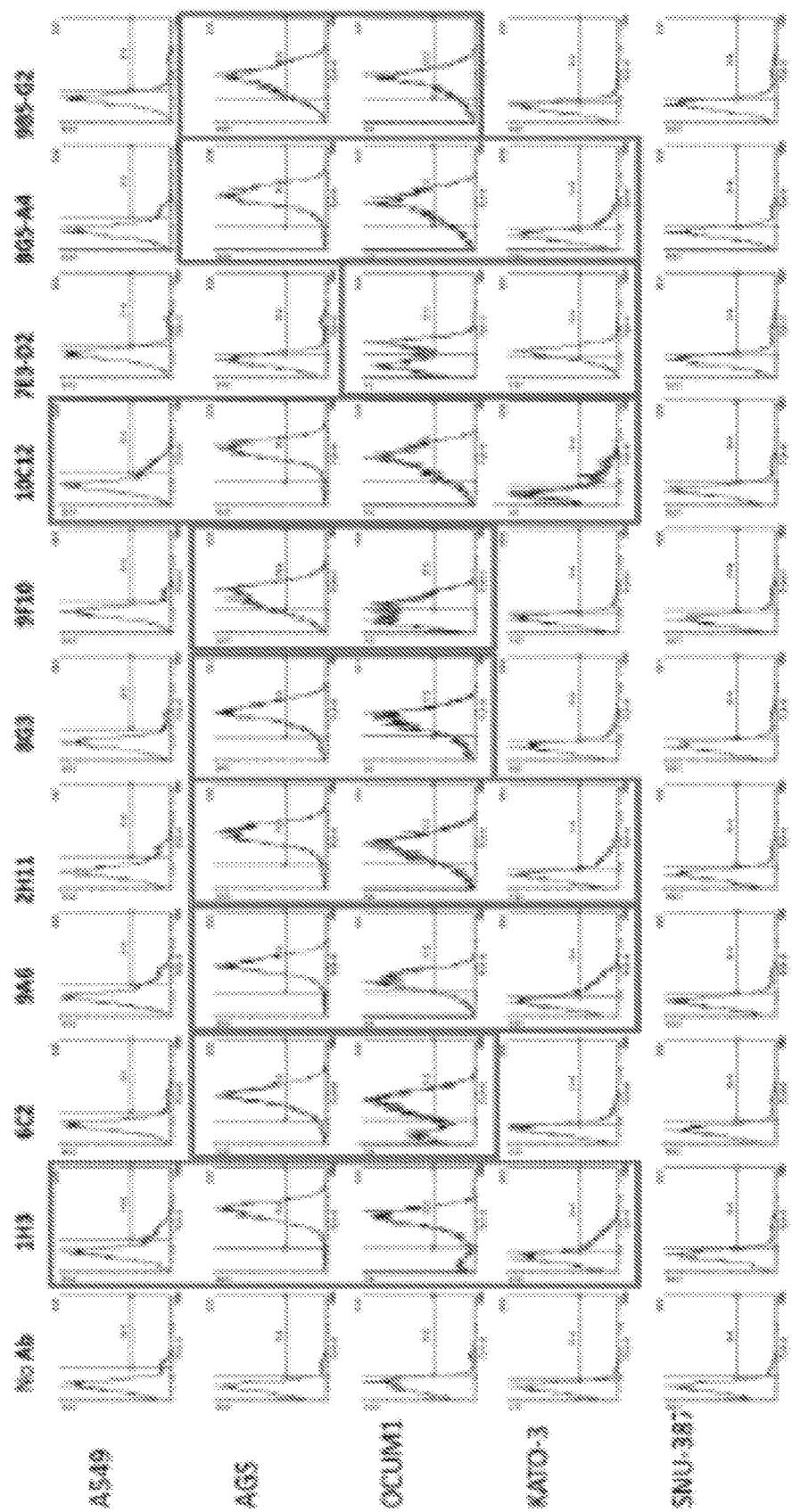
FIG. 21 presents examples of CDH17 monoclonal antibodies and humanized Lic3 scFvFc (h3scFv) binding to tumor cell lines as determined by FACS. Surprisingly many CDH17 monoclonal antibodies demonstrated different patterns of binding to the different CDH17 expressing tumor cell lines (red boxes).

In another aspect, antibodies were identified that bound to D1, D6 and D1 and D6 domains that have been implicated in CDH17 dependent homotypic and heterotypic interactions. The binding of CDH17 antibodies to CDH17 positive tumor cell lines, by flow cytometry, yielded unanticipated results (FIG. 21). Many different binding profiles were observed suggesting that there are different forms of CDH17 expressed in a cell type-specific manner. This notion is further supported by differential binding of CDH17 antibodies to recombinant CDH17 produced in CHO cells versus 293 F cells. Therefore, these novel CDH17 antibodies may be used to selectively target CDH17 expressed in one tissue and not another.

Figure 22:
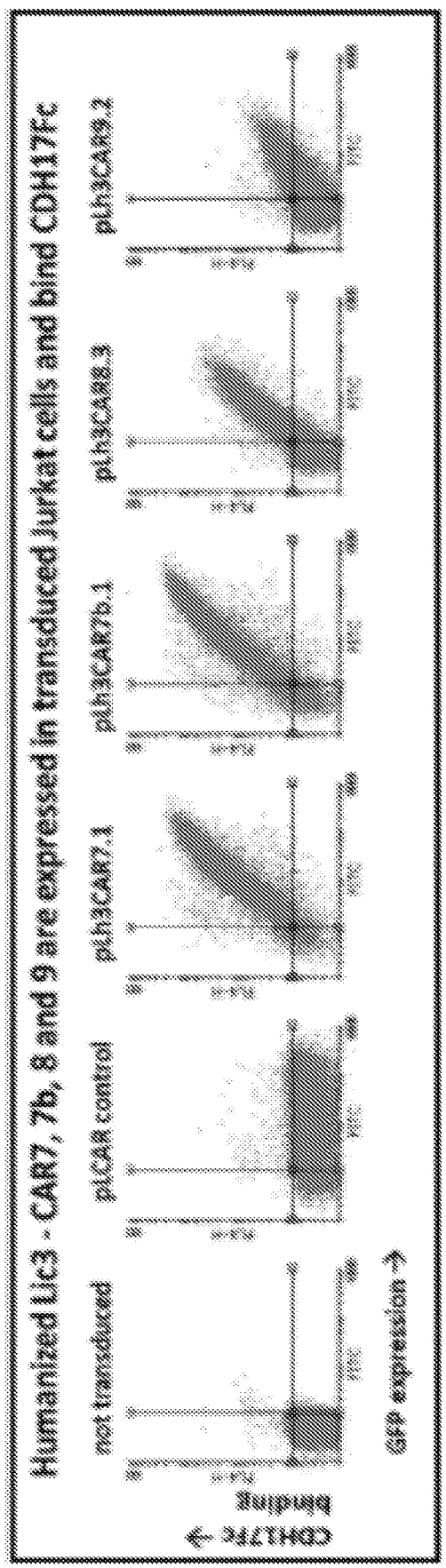
FIG. 22 presents the design (a) and analysis (b) of second-generation CAR, including an amino acid sequence of hLic3 CAR7a (SEQ ID NO. 25), hLic3 CAR7b (SEQ ID NO. 26), hLic3 CAR8 (SEQ ID NO. 27), and hLic3 CARS (SEQ ID NO. 28).
Figure 23:
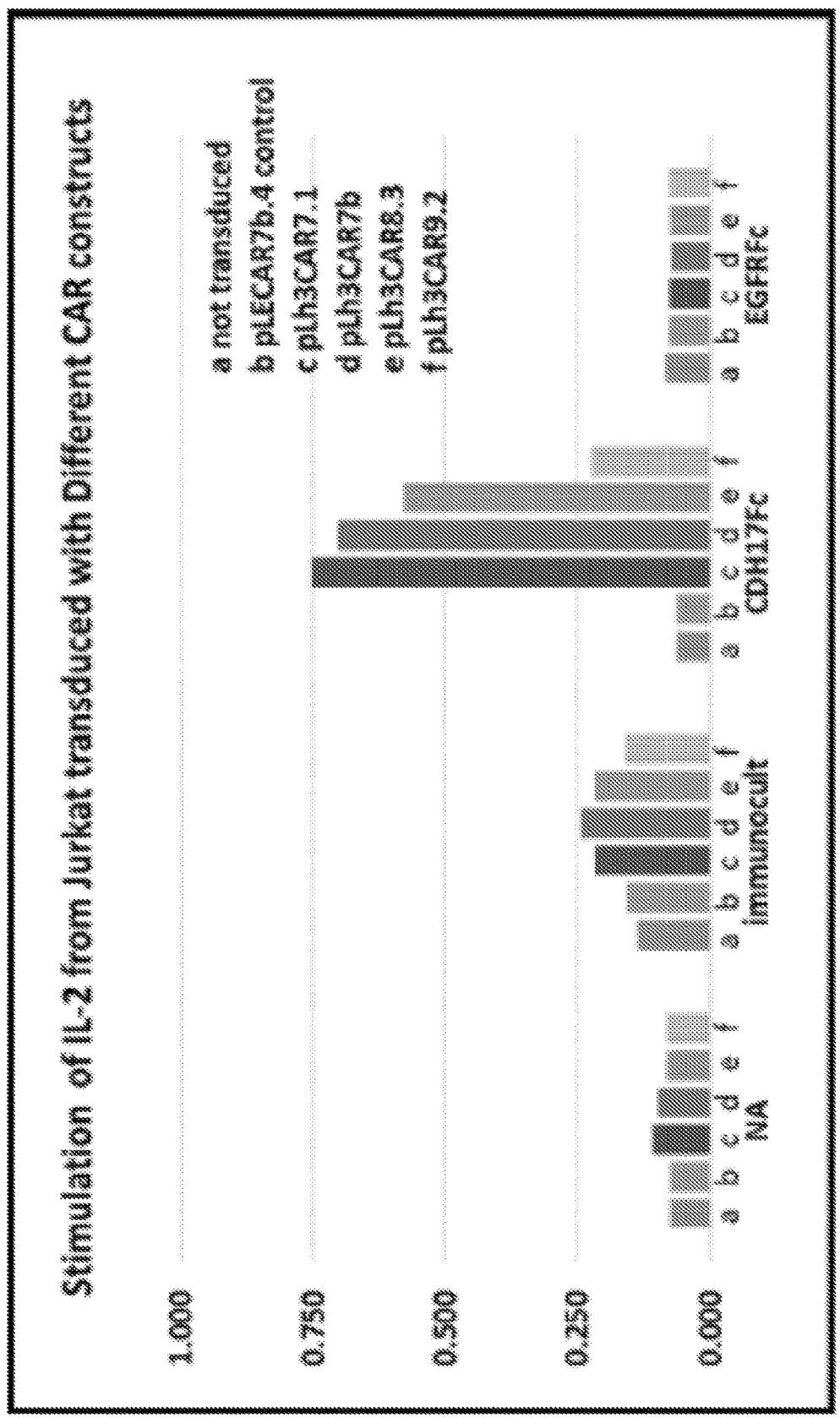
FIG. 23 presents IL2 production as the function of signaling.

In some embodiments, a second-generation CAR was designed and analyzed, in which CAR7, 7b, 8 and 9. CARs were constructed with humanized Lic3 scFv, CD8 or IgG1 hinges, CD8 or CD28 transmembrane domains, CD137 or CD28 endodomains and CD3zeta (isoforms ½ or ¾) endodomains (FIG. 22A). Jurkat cells at 4 days post-lentivirus transduction were analyzed by FACS analysis, which shows the GFP expression and CAR expression by soluble recombinant CDH17Fc binding (FIG. 22B). The CDH17 binding to CARs was determined by using an anti-Fc fluorochrome conjugate. Furthermore, Jurkat cells expressing different CARs were seeded in 96 well plates coated with CDH17Fc, EGFRFc (control), or no protein (NA). Immunocult (CD3-CD28 complex) was added to some uncoated wells containing Jurkat cells. Il-2levels in the culture media was measured by ELISA after 48 hours of stimulation (FIG. 23), indicating that IL2 production can be assessed as the function of signaling.

In some embodiments, CDH17 antibodies may antagonize the binding of the RGD site in CDH17 domain 6 to integrins including alpha2beta1.

In another aspect, bispecific antibodies having specificity for CDH17 are disclosed. The bispecific antibodies may have at least one of the following features including, without limitation, killing tumor cells by linking tumor cell (CDH17) with cytotoxic T or NK cell receptors (e.g. CDH17/CD3) in a manner to activate cellular cytotoxicity, increasing anti-cancer activity by binding a lymphoid/NK/monocytic cell activator (e.g. 4-1BB, OX40, CD27, CD40, TIM-1, CD28, HVEM, GITR, ICOS, IL12receptor, IL14 receptor) stimulating cytotoxicity or chemokine production and immune cell recruitment, blocking an immune checkpoint inhibitor (PD-1, TIM-3, LAG-3, TIGIT, CTLA-4, PD-L1, BTLA, VISTA), block an angiogenic factor (e.g. VEGF). CDH17 may be used in combination treatment with cytotoxic drugs (e.g. cisplatin, gemcitabine, irinotecan) or other anti-tumor antibodies.

In some embodiments, CDH17 specific scFv is engineered as second or third generation chimeric antigen receptors (CAR) to support T and NK cell-mediated tumor cell cytotoxicity (sequences and designs in FIG. 24-26). CDH17 specific CART and CAR NK cells may kill different types of solid tumors including but not limited to those of liver, gastric, colon, pancreatic, and lung. Hence, CDH17 may be used for various conditions related to, for example, liver and stomach cancers.

CDH17 is a prominent cancer biomarker overexpressed in both liver and stomach cancers but not in the normal healthy adult tissues. CDH17 is highly expressed in the metastatic phenotype of cancers, and blockage of CDH17 reduces markedly lung metastasis of HCC. Monoclonal antibodies targeting CDH17 marker are able to inhibit the growth of liver and stomach tumors. CDH17 humanized antibody can be used clinically to treat cancer patients with indication of CDH17 biomarker in the tumor tissues and/or in serum samples. Anti-CDH17 scFv molecules are selected to generate CART vector for proof-of-concept in vivo model studies.

Tumor antigens derived from clinical samples were selected for the antibodies with specificity directed against the tumor-restricted CDH17 epitopes. As such, both Lic5 and Lic3 mAbs were shown to bind tumor cells of HCC and GC only. By lowering and/or varying the antibody affinity (through computational modeling), CDH17-CAR-T cells will have enhanced differential binding to the tumor cell surface.

The most solid tumor is surrounded by vasculature and immune cells, which is characterized by an immune-suppressive environment. The presence of a large number of regulatory T cells and blockade of immune checkpoint factors (PD1 and TIM-3) in cancers will favor the immune tolerance conditions that might impact the effectiveness of CAR-T-cells. To address this issue, an anti-PD1/anti-Tim3 bispecific component in the CAR-T vehicle was created leading to the circumventing of the immune checkpoint barrier. In addition, once this anti-PD1/Tim3 component is engaged in the tumor microenvironment, it will switch to the anti-tumor cytotoxic activity of the CAR-T cells to enhance the efficacy and improve the safety.

Chimeric antigen receptor (CAR), also known as artificial T cell receptor, is engineered immunoreceptor, which is grafted the specificity of a monoclonal antibody onto a T cell facilitated by retroviral vectors. The CAR-engineered T cells can recognize and kill the cancer cells and demonstrate significant clinical benefits.

Chimeric IgG Fc-fusion protein for clinical applications is disclosed herein. Example chimeric IgG-fusion protein includes the soluble form of ICAM-1 and ICAM-2 for therapeutic intervention of autoimmune diseases and viral infections. The CAR-T vector is constructed with a scFv domain derived from a mAb, linker, and cytoplasmic domain, in which different generations of CAR-T vector have evolved from the simple form of CD3-zeta which contains 3 ITAMs (for activation and co-stimulatory signals) to the recent $3^{rd}$ generation containing CD28 and OX40 to provide proliferative/survival signals. From the CDH17-specific clones (Lic3 and Lic5) disclosed herein, the scFv segments were designed for cloning into the $3^{rd}$ generation of lentiviral based CAR-T vector.

EXAMPLES

The present disclosure is further described with reference to the following examples. These examples are provided for purposes of illustration only and are not intended to be limiting unless otherwise specified. Thus, the present disclosure should in no way be construed as being limited to the following examples, but rather, should be construed to encompass any and all variations which become evident as a result of the teaching provided herein.

Example 1. Study Design and Methodology

The effect of Lic5 alone or in combination with cisplatin or epirubicin on tumor growth inhibition and animal survival were tested using an orthotopic tumor xenograft model. Human HCC cell lines MHCC97-L (97L) and PLC/PRF/5 (PLC) were used. Single Lic5, cisplatin and epirubicin treatment inhibited the growth of cultured HCC cells using cell proliferation assay, while more significant reductions were observed when cisplatin or epirubicin was used together with Lic5. Similar trends of growth inhibition were observed when the same experimental grouping was applied to treat orthotopic tumor-bearing nude mice.

Treatment of Lic5 enhanced survivals of orthotopic tumor-bearing nude mice when compared to the control group. Among all experimental groups, combined Lic5 and epirubicin group yielded the best survival. For next phase antibody humanization, the complementarity determining regions (CDRs) on variable regions on the light and heavy chain of Lic5 were identified. Both cell lines were cultured in Dulbecco's Modified Eagle Medium (DMEM) (Life Technologies, Grand Island, N.Y., USA) supplemented with 10% heat-inactivated fetal bovine serum (FBS) (Life Technologies), 100 units/ml penicillin and streptomycin (Life Technologies). Cultured cells were maintained in a humidified atmosphere at 37° C. with 5% carbon dioxide.

Example 2. Production and Characterization of Lic5, an In-House Monoclonal Antibody Against CDH17

An in-house hybridoma cell line secreting Lic5 was generated as described [5]. Hybridoma cells were maintained in DMEM supplemented with 10% FBS and 100 units/ml penicillin and streptomycin. To collect Lic5, hybridoma cells were cultured in serum-free hybridoma-SFM (Life Technologies) for 6 days. The cultured supernatant was collected and purified using Protein G column (Life Technologies). The concentration of the purified Lic5 was estimated using RC DC Protein Assay (Bio-Rad, Hercules, Calif., USA). The purity of Lic5 was assessed by sodium dodecyl sulfate-polyacrylamide gel electrophoresis (SDS-PAGE) under reducing condition, followed by Coomassie Blue staining. Immunoreactivity and specificity of Lic5 were confirmed by western blot using 97L cell lysate and by immunohistochemistry using paraffin-embedded human HCC tissue. The use of clinical specimen for research was approved by the Institutional Review Board of The University of Hong Kong/Hospital Authority Hong Kong West Cluster (HKU/HA HKW IRB). The procedures for SDS-PAGE, Coomassie Blue staining and western blot were routinely performed, while the method for immunohistochemistry was described below.

Example 3. In Vitro Cell Proliferation Assay

A pre-determined number of 97L and PLC cells was seeded onto 96-well culture plates for 1 day. 150 ug/ml mouse IgG (Sigma-Aldrich, St Louis, Mo., USA) as a control for Lic5. After treatment, the proliferation of treated cells was measured using Cell Proliferation Kit I (Roche, Indianapolis, Ind., USA) and as described. In brief, MTT reagent was incubated with the treated cells for 4 hours. Colorimetric signals were then measured after addition of 10% SDS. Independent cell proliferation MTT assays were performed at least twice for result confirmation.

Example 4. Orthotopic Tumor Xenograft Model

Male nude mice were obtained from Laboratory Animal Unit of The University of Hong Kong, Hong Kong. Animals were housed in individually ventilated cages under a 12-hour light/12-hour dark cycle and with free access to autoclaved water and chow. Animal experiments performed in this study were approved by the Committee on the Use of Live Animals in Teaching and Research (CULATR) of our institute. To allow in vivo viewing of the growing orthotopic liver tumors, previously established luciferase-labelled 97L cell line was used. 5×106 luciferase-labeled 97L cells were injected subcutaneously into nude mice to allow the growth of the subcutaneous tumors. These subcutaneous tumors were harvested when their sizes reached 200-300 mm3 and used as tumor seeds to establish orthotopic liver tumors in a separate group of nude mice following the standard procedure. Five days after orthotopic tumor implantation, mice received different treatments as following via intraperitoneal administration 3 times/week for 3 weeks (10-11 mice in each group): (1) 6 mg/kg Lic5; (2) 1 mg/kg cisplatin; (3) 1 mg/kg epirubicin; (4) combined treatment of Lic5 and cisplatin; (5) combined treatment of Lic5 and epirubicin; (6) 6 mg/kg mouse IgG as Lic5 control. Every week after treatment, orthotopic tumor growth and metastasis were monitored by live imaging in an IVIS 100 In Vivo Imaging System (Perkin Elmer, Waltham, Mass., USA) after intraperitoneal injection of 150 mg/kg potassium luciferin (Gold Biotechnology, St Louis, Mo., USA). For each measurement, a net photon count was obtained for each tumor. At the end of the experiment, orthotopic tumors were collected and subjected to formalin fixation and paraffin embedding.

Example 5. Animal Survival Study

Orthotopic liver tumors were established as above using 97L cells. Orthotopic tumor-bearing mice received the following treatments intraperitoneally 3 times/week for 3 weeks (11-15 mice in each group): (1) 8 mg/kg Lic5; (2) 1 mg/kg cisplatin; (3) 1 mg/kg epirubicin; (4) combined treatment of Lic5 and cisplatin; (5) combined treatment of Lic5 and epirubicin; (6) 8 mg/kg mouse IgG as Lic5 control. Animal survival was continuously monitored till 6 weeks after treatment.

Example 6. Immunohistochemistry

Immunohistochemistry was performed on paraffin-embedded orthotopic tumor xenografts and human HCC specimen as described. In brief, 6 um sections were prepared for deparaffinization and rehydration. After antigen retrieval and hydrogen peroxide treatment, sections were blocked with 3% bovine serum albumin before staining with mouse monoclonal antibody against alpha-catenin (1:200; BD Biosciences, San Jose, Calif., USA) and Lic5 (0.0625 ug/ml) overnight at 4° C. Signals were detected using EnVision+ System-HRP Labelled Polymer Anti-mouse (Dako, Carpinteria, Calif., USA) and visualized using Liquid DAB+ Substrate Chromogen System (Dako). Counterstaining was performed using hematoxylin. Images were captured using DXM1200F digital camera (Nikon, Melville, N.Y., USA).

Example 7. Cloning of Variable Regions of Lic5

Total RNA was extracted from Lic5-secreting hybridoma cells using TRIzol reagent (Life Technologies) and converted to cDNA using SuperScript III First-Strand Synthesis System (Life Technologies). Variable region cDNA fragments from heavy chain and light chain of Lic5 were amplified using Ig-Primer Set (Novagen, Germany) and Platinum Taq DNA Polymerase High Fidelity (Life Technologies). Variable region of light chain was amplified by the 5' variable region primer (5'-ATGGAGACAGACACACTCCTGCTAT-3') and 3' primer on the constant region, while variable region of heavy chain was obtained by the 5' variable region primer (5'-ATGAACTTYGGGYT-SAGMTTGRTTT-3', in which Y=C/T, S=C/G, M=A/C, and R=A/G) and 3' primer on the constant region. PCR products after resolving on a 1.5% agarose gel were purified and sequenced (BGI, Hong Kong).

Example 8. Identification of CDR of Lic5

The nucleotide sequences of variable region of heavy chain and light chain of Lic5 were used to derive the amino acid sequences, which were then numbered according to Kabat numbering scheme. CDR was identified according to Kabat definition (www.bioinf.org.uk).

Example 9. Statistical Analyses

Statistical analyses were performed using SPSS version 19 (SPSS Inc., Chicago, Ill., USA). Data presented in bar chart are expressed as mean ±SD/SEM. Student's t-test was used to calculate the significance of the difference between treatment groups and control group in both cell proliferation MTT assay and animal tumor xenograft experiments. Kaplan-Meier method was employed for survival analyses, while the differences in survival were calculated using log-rank test. A p-value of less than 0.05 was considered statistically significant.

Figure 30:
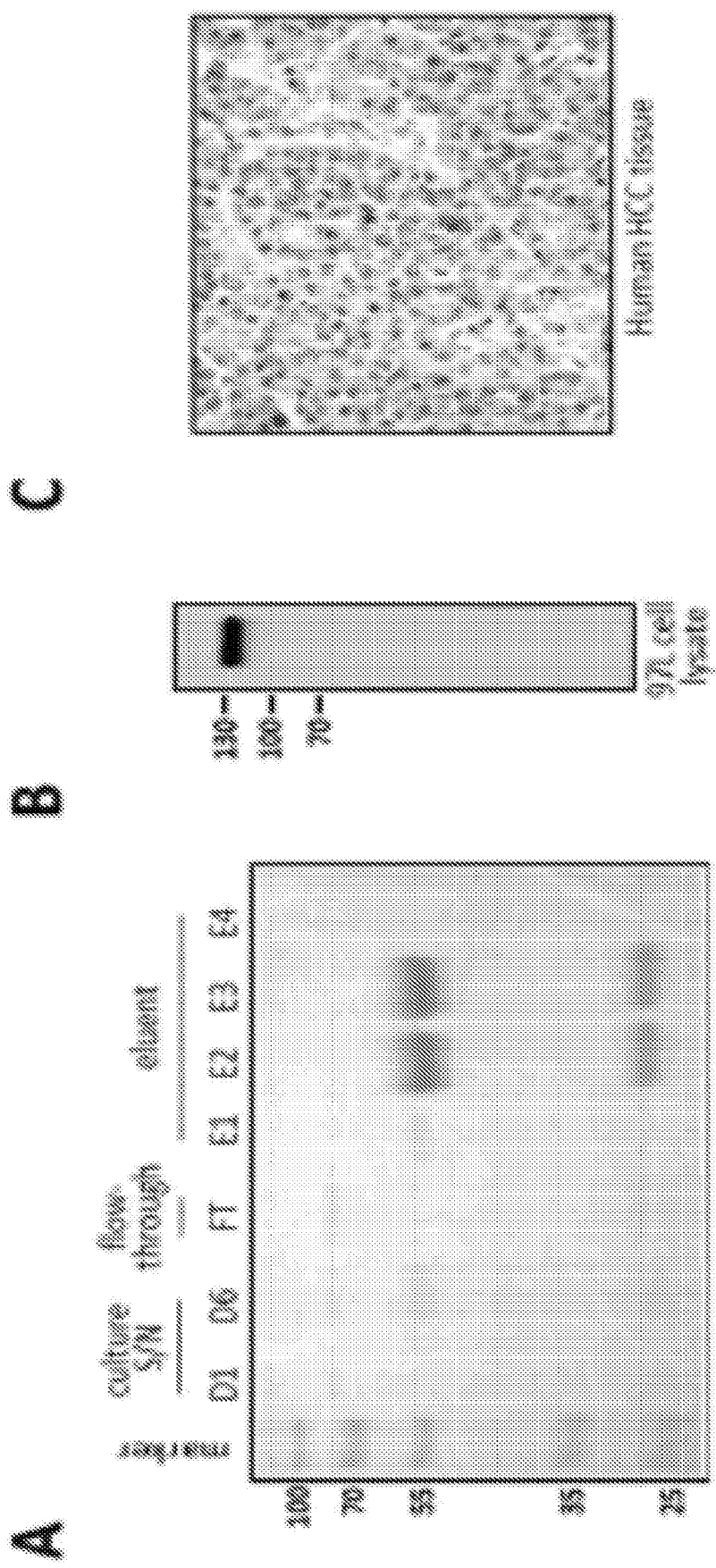
FIG. 30. shows Lic5 purification and characterization

Example 10. Establishment and Purifying Large Quantity of Lic5 from Hybridoma Cell Culture Supernatant To obtain Lic5 with high purity and quantity for in vitro and in vivo experiments, Lic5-secreting hybridoma cells were cultured in serum-free medium. Purifying Lic5 has thus far achieved a good antibody purity and yield for establishing a pipeline. Coomassie Blue staining result revealed two prominent bands of about 55 and 27 kDa corresponding to the heavy and light chain of antibody on Day 6 culture supernatant, while these bands were not observed on Day 1 culture supernatant. With the presence of a detectable level of antibody, culture supernatant collected on Day 6 was subjected to Protein G affinity chromatography for antibody purification. Successful binding of antibody onto the Protein G column was confirmed when not detecting the presence of antibody in the flow-through after loading Day 6 culture supernatant onto the column. Antibody elution performed on different fractions (eluent E1 to E4) revealed the second and third elution fraction contained most abundant antibody. The two stained bands corresponding to the heavy and light chain of the antibody are the predominant bands detected on the protein gel, implicating our antibody purity with more than 90% (FIG. 30(A)). Using our antibody purification pipeline, a favorable antibody was collected amount of 23.88±6.96 mg Lic5 from each liter of culture supernatant collected on Day 6.

The purified Lic5 demonstrated high immunoreactivity against CDH17. A single band of about 120 kDa corresponding to the apparent molecular weight of CDH17 was detected in CDH17-expressing 97L cells when Lic5 was used as a primary antibody for western blot (FIG. 30(B)). When Lic5 was used for immunohistochemistry to detect CDH17 in human HCC tissue, discrete stains appeared at the cell membrane and cytoplasm (FIG. 30(C)). The immunohistochemical stains generated by using Lic5 in this study was similar to the previous report with the use of a commercial antibody against CDH17 for immunohistochemistry.

Example 11. Survival Benefit of Lic5

The chemosensitizing effect of Lic5 towards another chemotherapeutic drug epirubicin WAS examined. The drug testing with or without Lic5 in an orthotopic tumor xenograft model was performed.

Figure 31:
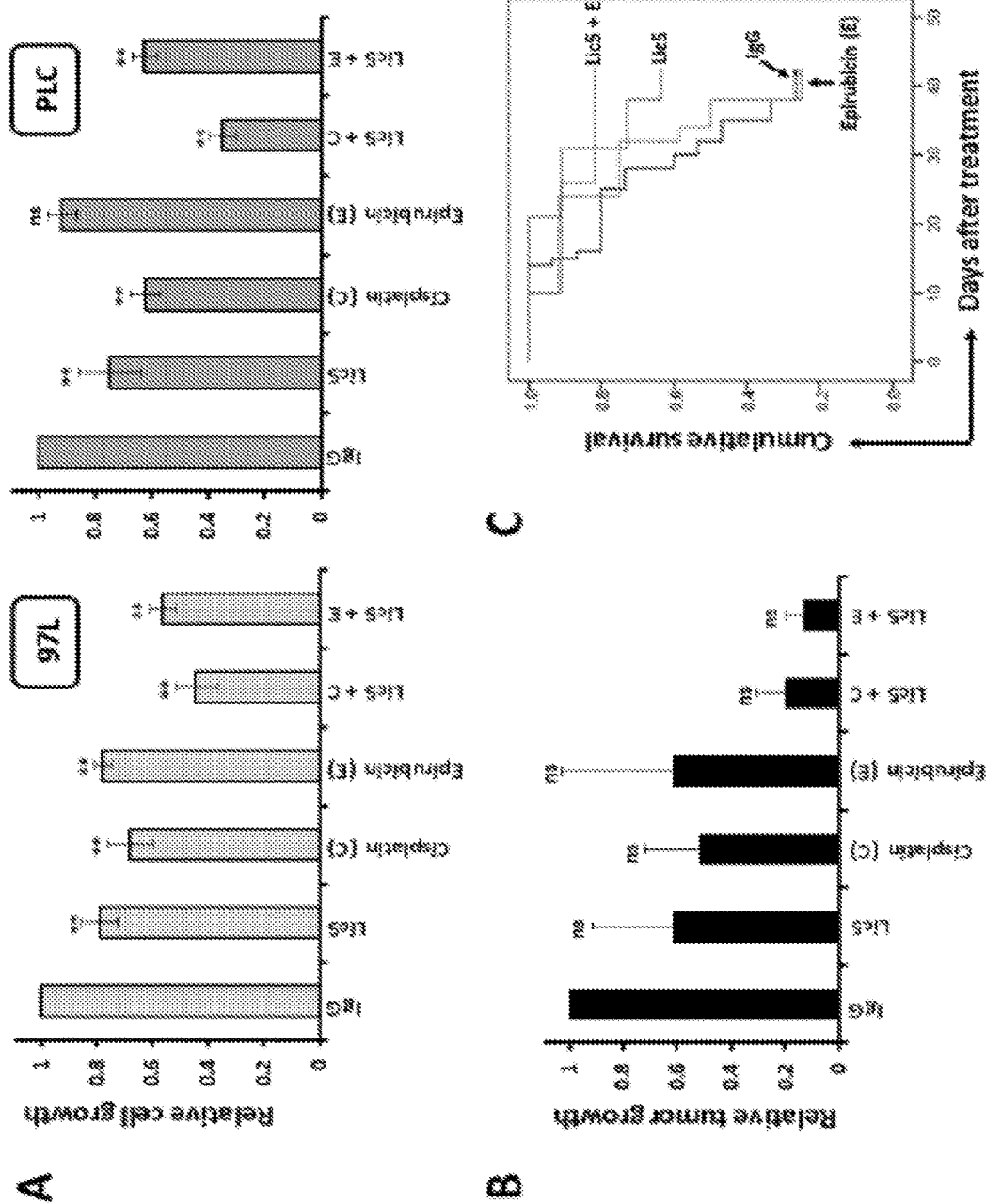
FIG. 31. shows the chemosensitizing effect of Lic5.

Before treating orthotopic tumor-bearing mice with the purified Lic5, the anti-tumor effect of Lic5 alone or combined with cisplatin or epirubicin in cultured HCC cell lines in vitro was examined using cell proliferation MTT assay (FIG. 31(A)). When cell proliferation assay was performed on cultured 97L cells, treatment with cisplatin and epirubicin for 2 days resulted in 31.6% and 21.9% growth inhibition, respectively. The combination with Lic5 further enhanced the growth inhibition effect by 1.74-fold for cisplatin and 1.98-fold for epirubicin, which led to a growth inhibition of 55.1% and 43.3%, respectively (FIG. 31(A), left panel). Similar growth inhibition was observed in cultured PLC cells, in which treatment with cisplatin resulted in 37.6% growth inhibition and combined treatment with Lic5 further increased the growth inhibition by 1.73-fold (65.2%). Unlike the significant growth inhibition of epirubicin on cultured 97L cells, this drug only inhibited the growth of cultured PLC cells by 8.1%. Likewise, its combination with Lic5 enhanced the growth inhibition by 4.62-fold and led to a significant inhibition of 37.4% (FIG. 31(B), right panel).

Lic5 was purified using Protein G affinity chromatography from culture supernatant of Lic5-secreting hybridoma cell line. FIG. 31(A) shows that, on the Coomassie Blue-stained gel, culture supernatant (culture S/N) from Day 6 (D6) contained higher antibody amount than Day 1 (D1). Two stained bands with sizes of about 55 kDa and 27 kDa corresponding to the heavy chain and light chain of antibody were visualized on the gel. No antibody was detected in the flow-through (FT) after passing the Day 6 culture supernatant on the Protein G column. Antibody elution was performed on 4 fractions (E1 to E4). The most abundant antibodies were eluted in fractions E2 and E3, which was collected and pooled. In addition, FIG. 31(A) shows that single treatment of Lic5, cisplatin or epirubicin for 2 days inhibited the growth of cultured 97L and PLC cells when compared to the mouse IgG-treated cells in cell proliferation MTT assay. Further growth inhibition was observed when the cultured cells were treated under combined treatment of Lic5 with cisplatin or epirubicin. Bars represent mean ±SD.

FIG. 31(B) shows that, using purified Lic5 for the western blot on 97L cell lysate, a single band corresponding to the apparent molecule weight of CDH17 was revealed. In FIG. 31(B), Luciferase-labelled 97L cells were used to establish orthotopic tumor xenografts in nude mice. Single and combined treatments of Lic5 with or without chemotherapeutic drugs cisplatin and epirubicin were applied to these animals for 3 weeks. The data shown are net photon count relative to the control IgG group obtained 3 weeks after treatment. Single treatment yielded tumor growth inhibition, while the further reduction in tumor growth was observed when Lic5 was combined with cisplatin or epirubicin. Bars represent mean+SEM.

FIG. 31(C) presents that, using purified Lic5 for immunohistochemistry on human HCC tissue, discrete stains corresponding to the membrane and cytoplasmic localizations of CDH17 were detected. In FIG. 31(C), Orthotopic tumor xenografts were established in nude mice using 97L cells. These animals were treated with single or combined treatment of Lic5 and epirubicin. Combined treatment of Lic5 and epirubicin led to most favorable survival as revealed in the Kaplan-Meier curve. A statistically significant difference in survivals was reached when the combined treatment group was compared with mouse IgG control group ($p=0.017$). Abbreviations used: C, cisplatin; E, epirubicin. **, $p<0.05$; ns, statistically not significant After the chemosensitizing effect of Lic5 towards cisplatin and epirubicin treatment on cultured HCC cells was confirmed by using cell proliferation MTT assay, the next step was to examine whether similar growth inhibition can be observed in an in vivo setting by animal tumor xenograft experiments. Luciferase-labelled 97L cells were used for developing orthotopic tumor xenografts for treatments as this enables live monitoring of tumor growth. When compared to IgG control group, cisplatin treatment inhibited the xenograft growth by 48.6%. Such treatment when combined with Lic5 further augmented the xenograft growth inhibition by 1.64-fold to 79.6%. Despite such inhibition, the combined treatment data did not yield a statistically significant value when compared to control group ($p=0.08$). For epirubicin, its combined treatment with Lic5 manifested a further reduction of xenograft growth from 37.9% for single epirubicin treatment to 86.4% (i.e. 2.28-fold). However, such drop in xenograft growth still did not reach a statistically significant value ($p=0.07$) (FIG. 31(B)). At the end of the experiment, the orthotopic tumors were collected for analyzing the expression and localization of alpha-catenin, which is known as a downstream molecule of CDH17 and is a key member of the Wnt signaling pathway. Both combined treatment of Lic5 with cisplatin or epirubicin reduced the overall expression and cytoplasmic localization of alpha-catenin when compared to the single treatment of chemotherapeutic drugs. Such immunohistochemical results further strengthen the tumor-suppressing effect mediated by Lic5 via its action on altering the expression and localization of alpha-catenin.

As shown in FIG. 31(B), a trend of tumor growth reduction was observed for every treatment group when compared to control group. The survival rate of orthotopic tumor-bearing mice for each treatment group versus control group was compared. The animal survival rate of Lic5 group reached 63.6%, which was much higher than that of the control group (26.6%). Although the survival rate between the control group and epirubicin group was similar (26.6% versus 25%), combined treatment of Lic5 and epirubicin led to the most significant increase in survival rate to 81% among all experimental groups when compared to control group (p=0.017) (FIG. 31(C)). However, such significant difference in survival for cisplatin group and cisplatin with Lic5 group did not reach any statistically significant values when compared to control group. Taken together, this set of animal experiments has demonstrated the chemosensitizing effect of Lic5 in particular for epirubicin on tumor growth inhibition and survival rate induction.

Example 13. Identification of CDR on Variable Regions of Lic5

Figure 32:
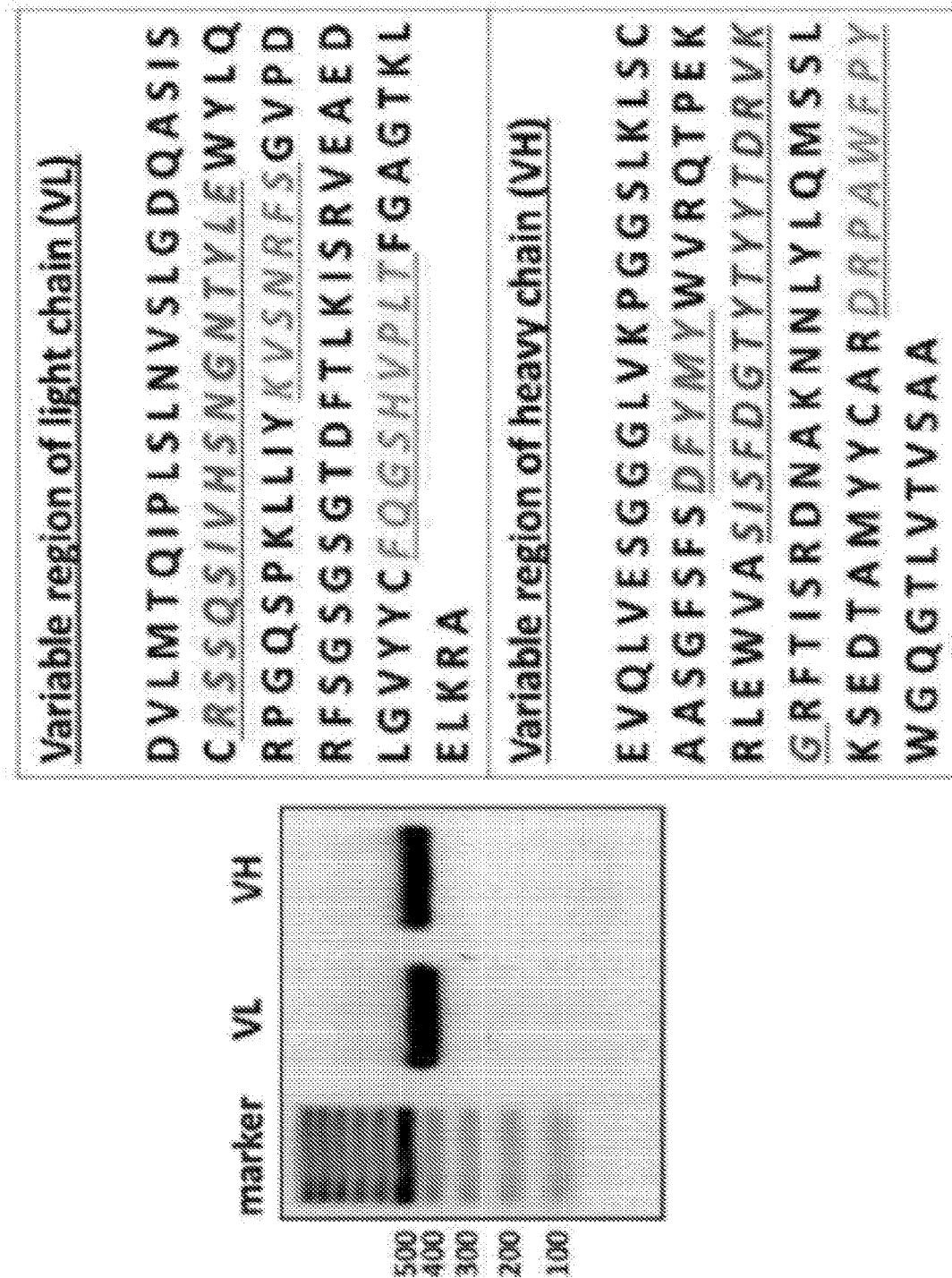
FIG. 32. shows amino acid sequences of the variable regions of the light chain and heavy chain of Lic5.

Each monoclonal antibody has its unique variable regions on heavy chain and light chain, for which each of them is composed of a sequence of amino acids that determines the antigen binding property of this antibody. To obtain the variable region sequences from heavy chain and light chain of Lic5, each variable region was amplified using discrete primer pairs (FIG. 32, left panel). After Sanger sequencing of the amplified products, the nucleotide sequences were translated into amino acid sequences by in silico method. Kabat numbering scheme and CDR definition were employed to identify the three CDRs on the variable regions of heavy chain and light chain of Lic5 using the deduced amino acid sequences (FIG. 32, right panel). PCR followed by Sanger sequencing were used to obtain the variable region sequences of light chain and heavy chain of Lic5 from cDNA prepared from Lic5-secreting hybridoma cells (FIG. 32, left panel). Based on the Kabat numbering scheme and CDR definition, the six CDRs on the two variable regions (VL: SEQ ID NO. 29 and VH: SEQ ID NO. 30) were identified and highlighted in different colors (FIG. 32, right panel)

The results from the examples have demonstrated the anti-tumor and chemosensitizing effects of Lic5 in treating HCC xenografts, showing that the monoclonal antibodies disclosed herein may be useful to treat other cancers in addition to HCC. Lic5 was a monoclonal antibody produced in parallel with Lic3using recombinant ectodomain 1-2 of CDH17 as an immunogen. Lic5 targets the extracellular region of CDH17; it can bind to intact form or carboxyl-terminal truncated form of CDH17 when used for therapeutic purpose. Therefore, Lic5 can be used to target other cancers with CDH17 overexpression. In addition to HCC, a number of cancers are found overexpressing CDH17, which include gastric adenocarcinoma, esophageal adenocarcinoma, and colorectal cancers. Among these cancer types, CDH17 overexpression was present in the majority of colorectal and esophageal adenocarcinoma cancers. As such, these CDH17-overexpressing cancers may be susceptible to the action of Lic5. Several studies performing CDH17 suppression counteracted tumorigenesis as manifested by reduced growth of cultured cells or tumor xenografts after treatment. Thus, targeting CDH17 to counteract tumorigenesis works well in other cancers overexpressing CDH17 in addition to HCC.

The results from the examples show that CDH17 seems to be linked with α-catenin-associated network. In one embodiment, targeting CDH17 using Lic5 inactivates CDH17/α-catenin axis by interfering with the expression and localization of the axis components such as α-catenin. In another cancer type, CDH17 was bridged to integrin-related pathway during colorectal tumorigenesis because of the intrinsic integrin-binding affinity of CDH17. CDH17 also affects two other tumorigenic pathways related to Ras/Raf/MEK/ERK and NFγB, such that its suppression inactivated these pathways in gastric cancer. Given these observations, it remains to be determined whether Lic5 could also block these pathways as a mean to suppress tumorigenesis.

In addition to testing the anti-tumor effects of Lic5, three CDRs on each variable region on heavy and light chains of Lic5 were identified. These CDRs are responsible for determining antibody binding affinity and specificity.

Pharmaceutical Compositions

The term "effective amount" refers to an amount of a drug effective to achieve a desired effect, e.g., to ameliorate disease in a subject. Where the disease is cancer, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is cancer, the effective amount of the drug may alternatively do one or more of the following when administered to a subject: slow or stop tumor growth, reduce tumor size (for example, volume or mass), relieve to some extent one or more of the symptoms associated with the cancer, extend progression-free survival, result in an objective response (including, for example, a partial response or a complete response), and increase overall survival time. To the extent the drug may prevent growth and/or kill existing cancer cells, it is cytostatic and/or cytotoxic.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

Similarly, persons skilled in the art have the ability to determine the effective amount or concentration of the antibodies disclosed therein to effective treat a condition such as cancer. Other parameters such as the proportions of the various components of the pharmaceutical composition, the administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description.

In summary, the novel panel of CDH17 antibodies, whose variable domains are derived from CDH17 mAb, will enable the generation of unique CARs for cancer treatment. The cell type specificity of CDH17 antibodies may enable more specific targeting of CDH17 expressing tumor cells relative to CDH17 expressed in normal cells or tissues. T cells or NK cells expressing two CARs may also be generated in which one CAR is more specific for CDH17 on tumor cells and the second CAR is moderately specific for a tumor associated antigen (TAA) on the same tumor cells. The combinatorial specificity is enabling a more selective targeting of a tumor cell signature. Alternatively, a CDH17 CAR may support more specific targeting of a moderately specific tumor specific TAA CAR through a different mechanism. For example, a moderately specific colon or gastric cancer TAA CAR may be fused to a CD3zeta endodomain. This first generation CAR may not support a robust killing response and has a short in vivo half-life of 1 to several weeks. A CDH17 CAR may be coexpressed that is fused to CD28 or CD28 and CD137 endodomains which will provide a strong costimulatory signal to the $1^{st}$ generation CAR. The CDH17 CAR will bind and activate a robust tumor-killing response in colon and stomach where CDH17 is normally expressed. The co-expressed $1^{st}$ generation CAR would be selected for binding a target that is not normally expressed in colon or stomach (or other tissue where CDH17 is normally expressed) and hence would be selectively activated to kill colon or stomach cancer cells.

While the disclosure has been described with reference to particular embodiments, it will be understood that the embodiments are illustrative and that the disclosure scope is not so limited. Alternative embodiments of the present disclosure will become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description.

The embodiments are merely for illustrating the present disclosure and are not intended to limit the scope of the present disclosure. It should be understood for persons in the technical field that certain modifications and improvements may be made and should be considered under the protection of the present disclosure without departing from the principles of the present disclosure.

What is claimed is:

1. An antibody having specificity for cadherin-17, comprising an amino acid sequence selected from the group consisting of SEQ ID NO(s): 1, 2, 17, and 19.

2. The antibody of claim 1, comprising a variable region of light chain (VL), a variable region of heavy chain (VH), wherein the VL comprises an amino acid sequence of SEQ ID NO: 1.

3. The antibody of claim 2, wherein the VH comprises an amino acid sequence of SEQ ID NO: 2.

4. The antibody of claim 1, further comprising a conjugated cytotoxic moiety, wherein the conjugated cytotoxic moiety comprises irinotecan, auristatins, PBDs, maytansines, amantins, spliceosome inhibitors, a chemotherapeutic agent, or a combination thereof.

5. The antibody of claim 1, wherein the antibody is a bispecific monoclonal antibody.

6. The antibody of claim 5, having specificity for a cell receptor from a cytotoxic T or NK cell, wherein the cell receptor comprises 4-1BB, OX40, CD27, CD40, TIM-1, CD28, HVEM, GITR, ICOS, IL12receptor, IL14 receptor, or a combination thereof.

7. The antibody of claim 5, comprising a first single-chain variable fragment (ScFv) having specificity for cadherin-17 and a second sing-chain variable fragment (ScFv) having specificity for CD3, wherein the first ScFv comprises a first VH and a first VL, the second ScFv comprises a second VH and a second VL.

8. The antibody of claim 7, wherein the first VH comprises an amino acid sequence of SEQ ID NO: 2.

9. The antibody of claim 7, wherein the first VL comprises an amino acid sequence of SEQ ID NO: 1.

10. The antibody of claim 7, wherein the second VH and the second VL comprises the VH and the VL, respectively, of the amino acid sequence of SEQ ID NO: 18.

11. The antibody of claim 1, having specificity for an immune checkpoint inhibitor, wherein the checkpoint inhibitor comprises PD-1, TIM-3, LAG-3, TIGIT, CTLA-4, PD-L1, BTLA, VISTA, or a combination thereof.

12. The antibody of claim 1, having specificity for an angiogenic factor, wherein the angiogenic factor comprises VEGF.

13. The antibody of claim 1, wherein the antibody is configured to antagonize the binding of the RGD site in cadherin-17 domain 6 to integrin, wherein the integrin comprises alpha2beta1.

14. An IgG heavy chain for an antibody, comprising an amino acid sequence having a sequence selected from SEQ ID NO: 2.

15. A light chain for an antibody, comprising an amino acid sequence having a sequence selected from SEQ ID NO: 1.

16. A variable region for an antibody, comprising a light chain variable region comprising SEQ ID NO: 1, and a heavy chain variable region comprising SEQ ID NO:2.

17. A scFv or Fab having specificity for cadherin-17, comprising an amino acid sequence selected from SEQ ID NO(s): 1, 2, 17, and 19, wherein the scFv or Fab has specificity for a cell receptor from a cytotoxic T or NK cell, an immune checkpoint inhibitor, or an angiogenic factor.

18. A pharmaceutical composition, comprising the antibody of claim 1 and a cytotoxic agent, wherein the cytotoxic agent comprises cisplatin, gemcitabine, irinotecan, or an anti-tumor antibody.

19. A method for treating a subject having a cadherin-1.7-expressing cancer, comprising administering to the subject an effective amount of the antibody of claim 1.

* * * * *